United States Patent
Sjölund

(10) Patent No.: US 11,056,243 B2
(45) Date of Patent: Jul. 6, 2021

(54) SYSTEMS AND METHODS FOR OPTIMIZING TREATMENT PLANNING

(71) Applicant: Elekta AB (Publ), Stockholm (SE)

(72) Inventor: Jens Olof Sjölund, Stockholm (SE)

(73) Assignee: Elekta AB (Publ), Stockholm (SE)

( * ) Notice: Subject to any disclaimer, the term of this patent is extended or adjusted under 35 U.S.C. 154(b) by 814 days.

(21) Appl. No.: 14/976,735

(22) Filed: Dec. 21, 2015

(65) Prior Publication Data

US 2017/0177812 A1 Jun. 22, 2017

(51) Int. Cl.
| | |
|---|---|
| G16H 20/40 | (2018.01) |
| G16H 70/20 | (2018.01) |
| G06N 20/00 | (2019.01) |
| A61N 5/10 | (2006.01) |
| G16H 50/70 | (2018.01) |
| G16H 30/40 | (2018.01) |
| G16H 50/20 | (2018.01) |

(52) U.S. Cl.
CPC ............ *G16H 70/20* (2018.01); *A61N 5/103* (2013.01); *A61N 5/1038* (2013.01); *G06N 20/00* (2019.01); *G16H 20/40* (2018.01); *G16H 30/40* (2018.01); *G16H 50/20* (2018.01); *G16H 50/70* (2018.01); *A61N 2005/1041* (2013.01)

(58) Field of Classification Search
CPC .............................................. G06Q 50/22–24
See application file for complete search history.

(56) References Cited

U.S. PATENT DOCUMENTS

| 10,046,177 B2 * | 8/2018 | Sjolund | G06N 7/005 |
| 2004/0146141 A1 * | 7/2004 | Svatos | A61N 5/103 |
| | | | 378/65 |

(Continued)

FOREIGN PATENT DOCUMENTS

| CN | 101689220 A | 3/2010 |
| CN | 104471608 A | 3/2015 |

(Continued)

OTHER PUBLICATIONS

PCT International Search Report and Written Opinion issued in PCT Application No. PCT/US2016/057795 dated Mar. 28, 2017 (18 pages).

(Continued)

*Primary Examiner* — Robert W Morgan
*Assistant Examiner* — Emily Huynh
(74) *Attorney, Agent, or Firm* — Finnegan, Henderson, Farabow, Garrett & Dunner, LLP

(57) ABSTRACT

The present disclosure relates to systems, methods, and computer-readable storage devices for radiotherapy treatment planning. For example, a method may generate a treatment plan for a patient. The method may receive training data reflecting radiotherapy treatment data. The training data may include a feature vector and a target vector. The method may further determine a training model based on the feature vector and the target vector. The method may further receive testing data associated with the patient. The testing data may include a descriptive feature vector. The method may further determine a therapy model based on the descriptive feature vector and the training model. The therapy model may be used to generate the treatment plan.

18 Claims, 10 Drawing Sheets

(56) References Cited

U.S. PATENT DOCUMENTS

| | | | |
|---|---|---|---|
| 2009/0234626 A1 | 9/2009 | Yu et al. | |
| 2009/0234628 A1 | 9/2009 | Yu et al. | |
| 2010/0057651 A1 | 3/2010 | Fung et al. | |
| 2014/0279725 A1 | 9/2014 | Kuusela et al. | |
| 2015/0043799 A1* | 2/2015 | Zhan | G06K 9/3233 382/131 |
| 2015/0095043 A1 | 4/2015 | Cordero Marcos et al. | |
| 2016/0129282 A1* | 5/2016 | Yin | G16H 20/40 600/1 |
| 2016/0140300 A1* | 5/2016 | Purdie | G06F 19/3481 705/2 |
| 2017/0004267 A1* | 1/2017 | Svatos | G06N 7/005 |
| 2017/0177822 A1* | 6/2017 | Fogel | G16H 10/60 |
| 2017/0259082 A1* | 9/2017 | Bzdusek | A61N 5/103 |
| 2017/0340900 A1* | 11/2017 | Moore | A61N 5/1031 |

FOREIGN PATENT DOCUMENTS

| | | |
|---|---|---|
| WO | WO 2014/187866 A1 | 11/2014 |
| WO | WO 2014/197994 A1 | 12/2014 |
| WO | WO 2014/205128 A1 | 12/2014 |
| WO | WO 2015/090459 A1 | 6/2015 |
| WO | WO 2015/176011 A1 | 11/2015 |
| WO | WO 2015/193776 A1 | 12/2015 |
| WO | WO 2016/081916 A1 | 5/2016 |

OTHER PUBLICATIONS

Andersson, Jesper LR, and Stamatios N. Sotiropoulos, "Non-parametric representation and prediction of single-and multi-shell diffusion-weighted MRI data using Gaussian processes." NeuroImage 122 (2015): 166-176.

Skarpman Munter, Johanna, and Jens Sjölund. "Dose-volume histogram prediction using density estimation." Physics in medicine and biology 60.17 (2015): 6923.

Zarepisheh, M., et al. "A moment-based approach for DVH-guided radiotherapy treatment plan optimization." Physics in medicine and biology 58.6 (2013): 1869.

Zarepisheh, Masoud, et al. "A multicriteria framework with voxel-dependent parameters for radiotherapy treatment plan optimizationa)." Medical physics 41.4 (2014a): 041705.

Zarepisheh, Masoud, et al. "A DVH-guided IMRT optimization algorithm for automatic treatment planning and adaptive radiotherapy replanning." Medical physics 41.6 (2014b): 061711.

J. Munter et al., "Dose-volume histogram prediction using density estimation," Phys. Med. Biol. vol. 60, No. 17, pp. 6923-6936, available online Jun. 25, 2015.

First Office Action and Search Report with Translation, from the China National Intellectual Property Administration for counterpart Chinese Application No. 201680081347.0, dated Dec. 25, 2019 (20 pages).

* cited by examiner

SYSTEMS AND METHODS FOR OPTIMIZING TREATMENT PLANNING

TECHNICAL FIELD

This disclosure relates generally to radiation therapy or radiotherapy. More specifically, this disclosure relates to systems and methods for developing a statistically optimal radiation therapy treatment plan to be used during radiotherapy.

BACKGROUND

Radiotherapy is used to treat cancers and other ailments in mammalian (e.g., human and animal) tissue. One such radiotherapy device is a Gamma Knife, which irradiates a patient with a large number of low-intensity gamma rays that converge with high intensity and high precision at a target (e.g., a tumor). Another radiotherapy device uses a linear accelerator, which irradiates a tumor with high-energy particles (e.g., electrons, and the like). Still another radiotherapy device, a cyclotron, uses protons and/or ions. The placement and dose of the radiation beam should be accurately controlled to ensure the tumor receives the prescribed radiation, and the placement of the beam should minimize damage to the surrounding healthy tissue, often called the organ(s) at risk (OARs). Treatment planning can be used to control radiation beam parameters, and a radiotherapy device effectuates a treatment by delivering a spatially varying dose distribution to the patient.

Treatment planning for radiotherapy modalities can be a patient specific, time-consuming, and resource-demanding task. Moreover, plan quality is subjective and highly dependent on the institution and the planners' skills and experiences. Automatic treatment planning has been introduced to facilitate this procedure. This is often done by employing a library of clinically approved and delivered reference plans of previously treated patients with similar medical characteristics to the patient undergoing treatment. One approach in the planning is to attempt to make the dose-volume histograms (DVH) similar for the treated patient and the reference plans. DVHs, however, are notoriously difficult to optimize and require the intensive work of iteratively solving a problem involving a surrogate function. In addition, DVHs compress an actual spatial dose distribution into one dimension and consequently lose significant information.

Some attempts have been made to optimize treatment plans on a voxel basis (e.g., "dose painting"). Dose painting can be used to specify different criteria for every voxel in the patient anatomy. However, instead of having about as many parameters as the number of relevant organs (e.g., ten), one ends up with about as many parameters as there are voxels (e.g., millions). In addition, voxel parameters are chosen such that reference plan DVH and treatment DVH are similar. But because DVH criteria lack spatial information, similar DVHs do not guarantee similar treatment plans and further computer-intensive calculations are often necessary to find an optimal plan.

Hence, there is a need of a method and system for generating optimal treatment plans to address the aforementioned issues.

SUMMARY

Certain embodiments of the present disclosure relate to a method for generating a treatment plan for a patient. The method may comprise receiving training data reflecting radiotherapy treatment data. The training data may include a feature vector and a target vector. The method may also comprise determining a training model based on the feature vector and the target vector of the received training data. The method may also comprise receiving testing data associated with the patient. The testing data may include a descriptive feature vector. The method may also comprise determining a therapy model based on the descriptive feature vector and the training model. Moreover, the method may comprise generating the treatment plan for the testing data based on the therapy model.

Certain embodiments of the present disclosure relate to a radiotherapy system. The radiotherapy system may comprise a memory storing computer executable instructions and a processor device communicatively coupled to the memory. The processor device may be configured to execute the computer executable instructions to receive training data reflecting radiotherapy treatment data. The training data may include a feature vector and a target vector. The processor device may also be configured to determine a training model based on the feature vector and the target vector of the received training data. The processor device may also be configured to receive testing data associated with the patient. The testing data may include a descriptive feature vector. The processor device may also be configured to determine a therapy model based on the descriptive feature vector and the training model. Moreover, the processor device may be configured to generate the treatment plan for the testing data based on the therapy model.

Certain embodiments of the present disclosure relate to one or more computer-readable storage devices having computer-executable instructions stored thereon causing a processor device to perform a method for generating a treatment plan for a patient. The computer-executable instructions may cause the processor device to receive training data reflecting therapy treatment data. The training data may include a feature vectors and a target vector. The computer-executable instructions may also cause the processor device to select a specific feature type and a specific target type of the received training data. The specific feature type may be predictive of the specific target type. The computer-executable instructions may also cause the processor device to aggregate feature vectors of the selected feature type and target vectors of the specific target type across a plurality of training data. The computer-executable instructions may also cause the processor device to determine a first conditional probability for the aggregated target vectors given the aggregated feature vectors. The computer-executable instructions may also cause the processor device to receive testing data associated with the patient. The testing data may include a descriptive feature vector. The computer-executable instructions may also cause the processor device to determine a second conditional probability based on the first conditional probability and the descriptive feature vector. The computer-executable instructions may also cause the processor device to determine a probability density function representing the second conditional probability. The computer-executable instructions may also cause the processor device to extract parameters of the probability density function. Moreover, the computer-executable instructions may also cause the processor device to minimize a convex optimization function based on the parameters of the probability density function to determine one or more treatment plan parameters.

Additional objects and advantages of the present disclosure will be set forth in part in the following detailed description, and in part will be obvious from the description, or may be learned by practice of the present disclosure. The objects and advantages of the present disclosure will be realized and attained by means of the elements and combinations particularly pointed out in the appended claims.

It is to be understood that the foregoing general description and the following detailed description are exemplary and explanatory only, and are not restrictive of the disclosed embodiments.

BRIEF DESCRIPTION OF THE DRAWINGS

The accompanying drawings, which comprise a part of this specification, illustrate several embodiments and, together with the description, serve to explain the disclosed principles. In the drawings.

DETAILED DESCRIPTION

Figure 1:
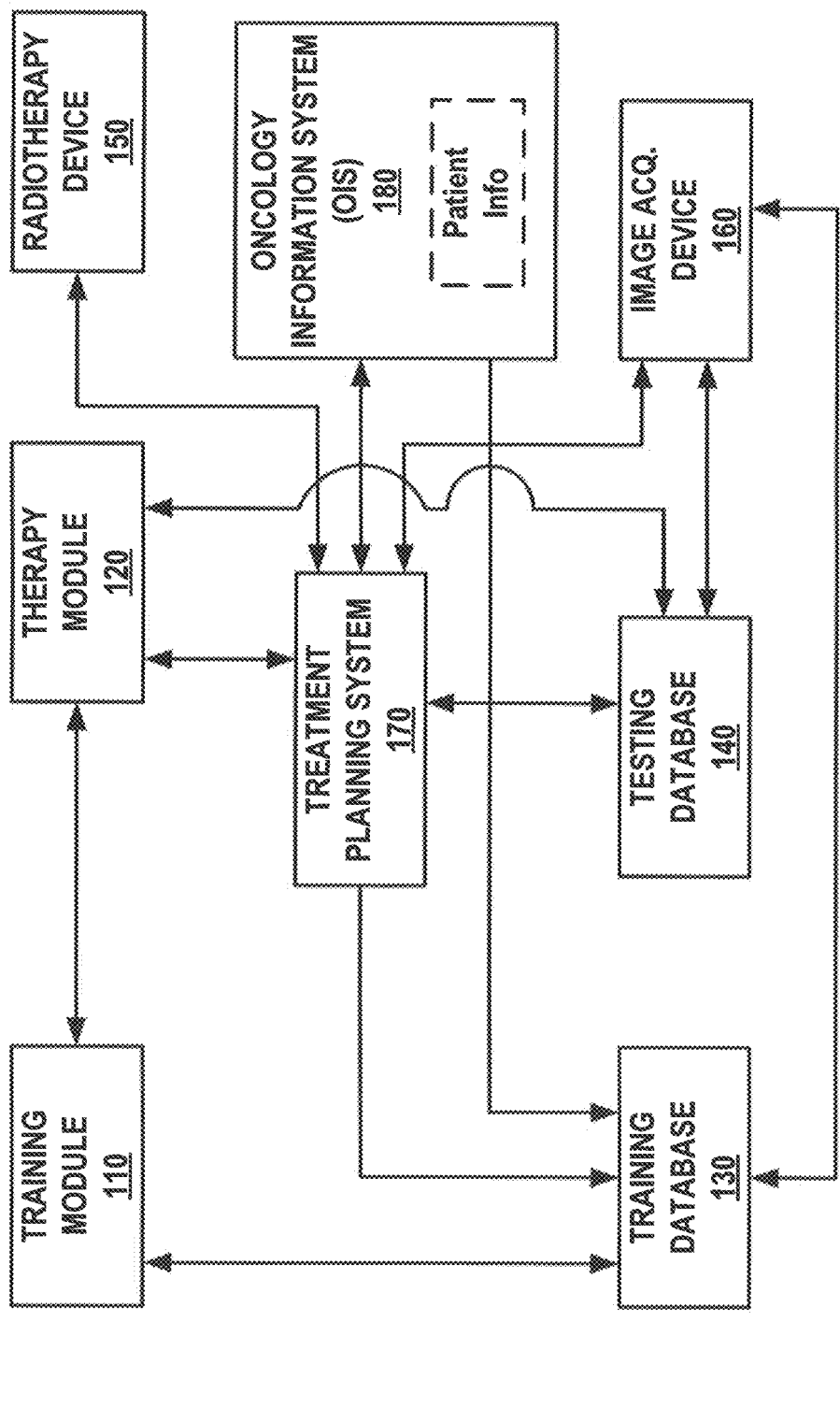
FIG. 1. illustrates an exemplary radiotherapy system for determining optimal treatment plans.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be interpreted as open ended, in that, an item or items following any one of these words is not meant to be an exhaustive listing of such item or items, or meant to be limited to only the listed item or items.

As used in this application and in the claims, the singular forms "a," "an," and "the" include the plural forms unless the context clearly dictates otherwise. Additionally, the term "includes" means "comprises." Further, the term "coupled" does not exclude the presence of intermediate elements between the coupled items.

The systems and methods described herein should not be construed as limiting in any way. Instead, the present disclosure is directed toward all novel and non-obvious features and aspects of the various disclosed embodiments, alone and in various combinations and sub-combinations with one another. The disclosed systems and methods are not limited to any specific aspect or feature or combinations thereof, nor do the disclosed systems and methods require that any one or more specific advantages be present or problems be solved. Any theories of operation are to facilitate explanation, but the disclosed systems, methods, and apparatus are not limited to such theories of operation.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

Systems and methods consistent with the present disclosure are directed to generating a treatment plan and/or validating a treatment plan using statistical information derived from past or previous treatment plans. Disclosed embodiments include systems and methods for creating a radiotherapy treatment plan ("treatment plan") using an optimization technique based on clinical and dosimetric objectives and constraints (e.g., voxel-based doses to the tumor and critical organs) for each patient undergoing radiation therapy. The treatment planning procedure may include using a three-dimensional image of the patient to identify a target region (e.g., the tumor, planning target volume (PTV), and the like) in the patient and to identify critical organs near the target region. In some embodiments, segmentation of the three-dimensional image may be performed to identify OARs and the target area (e.g., PTV) to be treated. A training model can be determined based on previous treatment plans from the same or different patients. The training model can be used to determine a therapy model for the current patient. A dose plan can be created using the therapy model for the patient indicating a desirable amount of radiation (e.g., dose distribution) to be received by the PTV (e.g., target) and/or the OARs. A treatment plan can be determined after optimizing plan parameters in an optimization model to ensure that a maximum dose is provided to the PTV while as low a dose as possible is provided to surrounding healthy tissue.

FIG. 1 illustrates an exemplary radiotherapy system 100. In some embodiments, radiotherapy system 100 includes a training module 110, a therapy module 120, a training database 130, a testing database 140, a radiotherapy device 150, and an image acquisition device 160. In some examples, radiotherapy system 100 includes a treatment planning system (TPS) 170 and an oncology information system (OIS) 180, which can provide patient information. In addition, radiotherapy system 100 may include output device(s) and input device(s). The output device(s) can be a display, printer, speaker, CD-writer, or another device that provides output from radiotherapy system 100. The input device(s) can be a touch input device such as a keyboard, mouse, pen, or trackball, a voice input device, a scanning device, or another device that provides input to the radiotherapy system 100. For audio, the input device(s) may be a sound card or similar device that accepts audio input in analog or digital form, or a CD-ROM reader that provides audio samples to the radiotherapy system 100.

Interconnections shown between elements are for illustrative purposes only. An interconnection mechanism such as a bus, controller, or network can interconnect the components of the radiotherapy system 100. Other connections can be available between elements not shown to be connected. Interconnections enable communication over a communication mechanism to storage devices (e.g., training database 130 and testing data 140) and/or computing entities (e.g., training module 110, therapy module 120, treatment planning system 170, radiotherapy device 150, image acquisition device 160, and/or OIS 180). The communication mechanism may convey information such as computer-executable instructions, audio/video or other information, or other data. By way of example, and not limitation, communication mechanisms include wired or wireless techniques implemented with an electrical, optical, RF, infrared, acoustic, or other carrier to communicate to another device, such as a memory bus interface, a processor bus interface, an Internet connection, a disk controller, and the like. The communication mechanisms can be configured by providing configuration parameters and/or sending signals to prepare the communication interface to provide a data signal describing the software content. The communication mechanisms can be accessed via one or more commands or signals sent to the communication interface.

As shown in FIG. 1, training module 110 may communicate with training database 130 to receive training data. Training database 130 may obtain training data from a treatment planning system 170, which may store data of previous radiotherapy treatment sessions (e.g., treatment planning system 170 stores previously developed treatment plans for a particular patient to be treated and for other patients, as well as other radiotherapy information). For example, treatment planning system 170 may provide information about a particular dose to be applied to a patient and other radiotherapy related information (e.g., type of therapy: such as image guided radiation therapy (IGRT), intensity modulated radiation therapy (IMRT), stereotactic radiotherapy; the number of beams; the beam angles; the dose per beam; and the like). In addition, the training data can also include image data to be obtained from image acquisition device 160. Image acquisition device 160 can include an MRI imaging device, a CT imaging device, a PET imaging device, an ultrasound device, a fluoroscopic device, a SPECT imaging device, or other medical imaging devices for obtaining one or more medical images of a patient. Image acquisition device 160 can provide the medical images to treatment planning system 170, testing database 140, and/or training database 130. For example, image acquisition device 160 can provide medical images (e.g., Magnetic Resonance Imaging (MRI) images, 3D MRI, 2D streaming MRI, 4D volumetric MRI, Computed Tomography (CT) images, Cone-Beam CT, Positron Emission Tomography (PET) images, functional MRI images (e.g., fMRI, DCE-MRI and diffusion MRI), X-ray images, fluoroscopic image, ultrasound images, radiotherapy portal images, single-photon emission computed tomography (SPECT) images, and the like) of a patient. In some embodiments, the training data can be collected from an OIS 180 (e.g., patient information, medical lab results, and the like).

In some embodiments, training module 110 and therapy module 120 may constitute a single data processing device. For example, training module 110 and therapy module 120 can be implemented as one or more software programs operating on the same hardware device. Similarly, training database 130 and testing database 140 can be implemented as a single database. For example, a single database can store both the training data and testing data. It is contemplated that any one of training module 110, therapy module 120, training database 130, and testing database 140 can be implemented as a standalone module.

In some embodiments, radiotherapy device 150 may be local with respect to therapy module 120. For example, radiotherapy device 150 and therapy module 120 can be located in the same room of a medical facility/clinic. In other embodiments, radiotherapy device 150 may be remote with respect to therapy module 120 and the data communication between radiotherapy device 150 and therapy module 120 via the treatment planning system 170 can be carried out through a network (e.g., a local area network (LAN); a wireless network; a cloud computing environment such as software as a service, platform as a service, infrastructure as a service; a client-server; a wide area network (WAN); and the like). Similarly, the communication links between other modules and/or devices, can also be implemented in a local or remote manner.

In some embodiments, the techniques and solutions described herein can be performed by software, hardware, or both of a computing environment, such as one or more computing devices. For example, computing devices include server computers, desktop computers, laptop computers, notebook computers, handheld devices, netbooks, tablet devices, mobile devices, PDAs, special purpose imaging devices, and other types of computing devices.

A suitable computing environment in which the described technologies, such as those described for FIG. 1, can be implemented include general-purpose or special-purpose computing environments. For example, the disclosed training module 110, therapy module 120, and/or treatment planning system 170 may be implemented using a computing device comprising a processing unit, memory, and storage storing computer-executable instructions. The disclosed technologies can also be implemented with other computer system configurations, including hand held devices, multiprocessor systems, microprocessor-based or programmable consumer electronics, network PCs, mini-computers, mainframe computers, a collection of client/server systems, and the like. The disclosed technologies can also be practiced in distributed computing environments where tasks are performed by remote processing devices that are linked through a communications network. In a distributed computing environment, program modules may be located in both local and remote memory storage devices.

The processing unit included, for example, in training module 110, therapy module 120, and/or treatment planning system 170 may execute computer-executable instructions and may be a real or a virtual processor device. In a multi-processing system, multiple processing units execute computer-executable instructions to increase processing power. The memory can be volatile memory (e.g., registers, cache, RAM), non-volatile memory (e.g., ROM, EEPROM, flash memory, etc.), or some combination of the two. The memory can store software implementing any of the technologies described herein. For example, the memory can store an operating system, training software implementing training module 110, and/or therapy software implementing therapy module 120. Typically, operating system software provides an operating environment for other software executing in the computing environment, and coordinates activities of the components of the computing environment.

The computing environment may have additional features. For example, the computing environment can include computer-readable storage devices. Computer-readable storage devices may be removable or non-removable, and include magnetic disks, magnetic tapes or cassettes, CD-ROMs, CD-RWs, DVDs, or any other tangible, computer-readable media, which can be used to store information and which can be accessed within the radiotherapy system 100. The computer-readable storage devices can store software containing instructions for any of the technologies described herein (e.g., training module 110, therapy module 120, and treatment planning system 170).

Disclosed embodiments may implement computer-executable instructions, such as those included in program modules and executed in a computing environment on a target real or virtual processor device. Program modules may include routines, programs, libraries, objects, classes, components, data structures, etc., that perform particular tasks or implement particular abstract data types. The functionality of the program modules may be combined or split between program modules as desired in various embodiments. Computer-executable instructions for program modules may be executed by a processing unit, as described above.

Various operations or functions of the example embodiments can be implemented as software code or instructions. Such content can be directly executable ("object" or "executable" form), source code, or difference code ("delta" or "patch" code). Software implementations of the embodiments described herein can be provided via an article of manufacture with the code or instructions stored thereon, or via a method of operating a communication interface to send data via the communication interface. A machine or computer-readable storage device can cause a machine to perform the functions or operations described, and includes any mechanism that stores information in a tangible form accessible by a machine (e.g., computing device, electronic system, and the like), such as recordable/non-recordable media (e.g., read only memory (ROM), random access memory (RAM), magnetic disk storage media, optical storage media, flash memory devices, and the like). Computer-readable storage devices store computer-readable instruction in a non-transitory manner and do not include signals per se.

With reference to FIG. 1, training module 110 may use training data to generate an output (e.g., a training model). Training data may include a plurality of previous treatment plans. In some embodiments, training data can be stored in training database 130. For example, the stored training data can include past radiotherapy treatments, diagnostic images, treatment images (dose maps), segmentation information, and the like, associated with one or more previous treatment plans. The training data can include a plurality of training samples. In some embodiments, a training sample includes a feature vector and a corresponding target vector.

A feature vector may include one or more feature elements (e.g., $x=[x_1, x_2, x_3, \ldots]$). A feature element is predictive and/or descriptive of a target element, as described herein. In an embodiment, each feature element indicates an observation of a medical image (e.g., provided by image acquisition device 160, stored in training database 130, stored in testing database 140, etc.) used in a past radiotherapy session (e.g., radiation therapy treatments).

In some embodiments, the feature vector can include arbitrary dimension and/or multiple types of data (e.g., continuous, ordinal, discrete, and the like). In some embodiments, the feature vector can include a distance to predetermined anatomical regions, such as the PTV(s) or the OAR(s) or the patient's surface. In some examples, the feature vector can include a signed distance x between a volume (e.g., a voxel) and an anatomical region, such as a PTV or the surface of the body part in the medical image, which can also be represented as voxels. Distances to multiple regions of interest can also be Included in the feature vector. In some embodiments, the feature vector can include global information, such as spatial coordinates of an anatomical region or a probability that an anatomical region includes a particular tissue type. In some embodiments, the feature vector can include features derived from a convolution of images with at least one linear filter (e.g., local phase, gradients, edge, or corner detectors). In some embodiments, the feature vector can include features derived by a transformation of one or more images (e.g., Fourier transform, Hilbert transform, Radon transform, distance transform, discrete cosine transform, wavelet transform, and the like). In each of these embodiments described above regarding the feature vector, a corresponding transformation to an output probability density can be applied.

In some embodiments, the feature vector can include information based on "information theoretical measures" (e.g., mutual information, normalized mutual information, entropy, Kullback-Leibler distance, and the like). In some embodiments, the feature vector can include a feature descriptor providing a higher-dimensional representation as used in the field of computer vision, such feature descriptor may include characteristics of a particular voxel of the image, such as SIFT (Scale-invariant feature transform), SURF (Speeded Up Robust Features), GLOH (Gradient Location and Orientation Histogram), or HOG (Histogram of Oriented Gradients). In another embodiment, the covariance/correlation between a plurality of image regions (e.g., two or more voxels) can be captured using a higher-dimensional representation. In some embodiments, the feature vector can include, for example, patient information such as age, gender, tumor size, a responsible physician and the like.

In another embodiment, the feature element can include patient specific information, responsible physician, organ or volume of interest segmentation data, functional organ modeling data (e.g., serial versus parallel organs, and appropriate dose response models), radiation dosage (e.g., also including dose-volume histogram (DVH) information), lab data (e.g., hemoglobin, platelets, cholesterol, triglycerides, creatinine, sodium, glucose, calcium, weight), vital signs (blood pressure, temperature, respiratory rate and the like), genomic data (e.g., genetic profiling), demographics (age, sex), other diseases affecting the patient (e.g., cardiovascular or respiratory disease, diabetes, radiation hypersensitivity syndromes and the like), medications and drug reactions, diet and lifestyle (e.g., smoking or non-smoking), environmental risk factors, tumor characteristics (histological type, tumor grade, hormone and other receptor status, tumor size, vascularity cell type, cancer staging, gleason score), previous treatments (e.g., surgeries, radiation, chemotherapy, hormone therapy), lymph node and distant metastases status, genetic/protein biomarkers (e.g., such as MYC, GADD45A, PPM1D, BBC3, CDKN1A, PLK3, XPC, AKT1, RELA, BCL2L1, PTEN, CDK1, XIAP, and the like), single nucleotide polymorphisms (SNP) analysis (e.g., XRCC1, XRCC3, APEX1, MDM2, TNFR, MTHFR, MTRR, VEGF, TGFβ, TNFα), texture descriptors (e.g., representations learned from deep learning), and the like. The feature vector can include one or more such feature elements, regardless of whether these feature elements are related to each other or not. In other words, the feature vector is predictive of the target vector.

A target vector can include one or more target elements (e.g., y=[y1, y2, y3, . . . ]). In some embodiments, each target element indicates a corresponding treatment plan outcome or parameter in a past radiotherapy session based on the observation(s) included in the feature vector. In some examples, the target element includes the dose d applied or received at a particular spatial location (e.g., a voxel). In another example, the target element includes a patient survival time based on observations such as a treatment type, treatment parameters, patient history, and/or patient anatomy. Additional examples of target elements include, but are not limited to, a normal tissue complication probability (NTCP), a region displacement probability during treatment, or a probability that a set of coordinates in a reference image is mapped to another set of coordinates in a target image. The target vector can include one or more such target elements, regardless of whether these output elements are related to each other or not.

In some embodiments, training module 110 can use training data to generate a training model. In some examples, the training model can be used by the therapy module 120. In some embodiments, the training model can represent statistical estimations or derivations drawn or calculated from training data (e.g., past treatment plans, treatment data, radiotherapy treatment plans, etc.). A training model can be a single model or a plurality of models. In some embodiments, a training model can be an output of training module 110. In other embodiments, a training model can be stored (e.g., in a memory, training database 130, or testing database 140) for later retrieval. Storage of the training model allows for faster retrieval when determining further treatment plans. In some embodiments, a training model can be generated by treatment planning system 170 or therapy module 120. In other embodiments, the training model can be sent to treatment planning system 170 or therapy module 120. Determining the one or more training model can be performed either offline or online. For example, the training model can be determined and stored before beginning the treatment process (e.g., offline) or the training model can be estimated in real-time (e.g., the training model is generated within specified time constraints) during the treatment process (e.g., online). In an embodiment, the training model can use training data from treatment plans for other patients. In another embodiment, training data can be used to adapt a treatment plan for a patient by comparing a plurality of previous treatment plans developed for the same patient. In another embodiment, training data can include treatment plans from a plurality of other patients with the same or similar medical diagnosis.

As described herein, training data can include training samples with a feature vector and a target vector. In some embodiments, the training model can be the conditional probability distribution of the target vector given the feature vector. In some examples, the conditional probability distribution of the target given the feature can be determined based on the joint probability distribution of the feature and target vectors and the feature probability distribution. In some examples, each set of training data can provide a single point in the resulting conditional probability. Aggregating the target and feature vectors across all treatment data can therefore provide a distribution of target vector elements given the feature vector elements.

In some embodiments where joint probability distributions (e.g., p(x,d), where x is a signed distance from a PTV boundary to a point in an OAR, and d is a dose) are determined, parametric methods, non-parametric methods, Monte Carlo based methods, machine learning methods, and the like can be used. Parametric methods assume a parameterized probability distribution and fit the distribution to the data. An example is the Gaussian mixture model. Non-parametric methods can estimate the density with minimum assumptions. Examples of non-parametric methods include the Kernel Density Estimation (KDE) algorithm, Gaussian process, and artificial neural networks, which model the unknown function as a weighted sum of several sigmoids, each of which is a function of all the relevant explanatory variables. Monte Carlo based methods can use repeated random sampling to estimate a probability distribution and can therefore be used in limited instances such as simulations. Machine learning methods can be extended to perform distribution estimation. Examples include transductive support vector machines (SVM), decision forests, random forests, regression models, and density estimation trees. Some of the distribution estimation methods (e.g., density estimation trees) can be particularly suitable for outlier detection or relevance determination. Monte Carlo based methods and machine learning methods (e.g., density estimation trees) can be better equipped to handle high-dimensional data.

In some examples, the joint probability distribution can be determined using a Gaussian process, a non-parametric density estimation method. For the Gaussian process, the joint probability of the feature (e.g., the voxel distance x) and the target (e.g., voxel dose d) for previous treatment plan image data (e.g., training data) x and d and an unobserved pair x* and d* is given by:

$$\begin{pmatrix} d \\ d^* \end{pmatrix} \sim N_{n+1}\left(0, \begin{pmatrix} K(x, x) + \sigma^2 I & k(x, x^*) \\ k(x^*, x) & k(x^*, x^*) \end{pmatrix}\right),$$

where K(x, x) is the n×x matrix with entries $K_{ij}=k(x_i, x_j)$, $\sigma^2$ is the variance of the observation error, and k(x, x*) is a covariance function. The covariance functions can be chosen, for example, as radial basis functions, spectral mixture (SM) kernel, Matérn covariance functions, rational-quadratic covariance functions and/or dot product covariance functions.

Using the chain rule of probability, a conditional probability can be determined from a joint probability. For example, a probability distribution associated with the feature in the training data can be determined. The probability distribution indicates a likelihood that the observation indicated by the feature is present in the training data. For example, for the signed distance x, the probability distribution p(x) for the entire set of treatment plan image data can be determined using a density estimation method, such as a Kernel Density Estimation (KDE) algorithm, Gaussian process, and the like. The conditional probability distribution can be described by the general equation:

$$p(d|x)=p(x,d)/p(x).$$

With reference to FIG. 1, therapy module 120 can use the one or more training models to determine a therapy model, (e.g., distribution parameters or other properties or outcomes) to generate a new treatment plan. In some embodiments, therapy module 120 can receive the one or more training models from training module 110. In some embodiments, therapy module 120 can receive testing data from testing database 140. Testing data can include a plurality of testing samples (e.g., elements). In some embodiments, a testing sample includes a feature vector (e.g., descriptive feature), as described herein. For example, the feature vector can be descriptive of the testing data, including information such as signed distance from a PTV to an OAR. In some embodiments, testing data can include place holders for target elements indicating an unobserved outcome corresponding to a feature element in testing data.

The testing data stored, for example, in testing database 140, can further include image data that may be obtained from image acquisition device 160. For example, image acquisition device 160 can provide medical images (e.g., MRI images, CT images, PET images, MRI images, X-ray images, ultrasound images, radiotherapy portal images, single-photon emission computed tomography (SPECT) images, and the like) of a patient.

The testing data and other radiotherapy information stored in testing database 140 can also be obtained from treatment planning system 170 and/or oncology information system 180. Testing data can be stored in testing database 140 before being received by therapy module 120.

Alternatively, during adaptive radiotherapy, the testing data can be received by therapy module 120 directly from radiotherapy device 150. In some embodiments, testing data may be retrieved from radiotherapy device 150 in an online mode while radiotherapy device 150 is in active operation of performing radiotherapy treatment (e.g., actual dose delivered to a patient). In other embodiments, testing data may be retrieved from radiotherapy device 150 in an offline mode, e.g., while radiotherapy device 130 is not in active operation of performing radiotherapy treatment.

A therapy model can represent statistical estimations or derivations of a conditional probability given a training model and testing data. In some embodiments, a therapy model can be determined directly from training data and testing data. A therapy model can be a single model or a plurality of models. In some embodiments, a therapy model can be an output of therapy module 120. In other embodiments, a therapy model can be stored (e.g., in memory, training database 130, or testing database 140) for later retrieval. Storage of the therapy model allows for faster retrieval when determining further treatment plans. In some embodiments, a therapy model can be generated by treatment planning system 170 or training module 110. In other embodiments, the therapy model can be sent to treatment planning system 170 or training module 110. Determining the one or more therapy model can be performed either offline or online. For example, the therapy model can be determined and stored before beginning the treatment process (e.g., offline) or the therapy model can be estimated in real-time during the treatment process (e.g., online). In some embodiment, the therapy model can use testing data from a patient undergoing current radiotherapy treatment.

As described herein, testing data can include a descriptive feature vector (e.g., signed distance $x^*$ from a voxel in an OAR in the testing data to a boundary of a PTV). In some examples, the therapy model describes a new conditional probability distribution derived from a particular target in the training data being associated with the descriptive feature in the testing data. In some embodiments, the derived conditional probability distribution for the testing data can be approximated by parametric or non-parametric distribution functions. For example, the derived conditional probability distribution for the testing data can be approximated by a log-concave distribution (e.g., Gaussian, Gamma, Laplace, Logistic, Subbotin, Uniform, Beta, and the like). In one example, the derived conditional probability distribution for the testing data can be approximated by a Gaussian distribution with a set of parameters (e.g., moments or cumulants) comprising a mean and standard deviation. In another example, the derived conditional probability distribution for the testing data can be approximated by a Gaussian process with a set of parameters (e.g., moments or cumulants) comprising a mean and covariance function. In some embodiments, the therapy model can be determined as the parameters of the density function that approximates the derived conditional probability distribution for the testing data given the training model.

In some embodiments, the therapy model can be determined by parametric or nonparametric density functions. In some examples, the density function is parametric (e.g., Gaussian, Gamma, and the like). For example, the probability density can follow a Gaussian (normal) distribution. The Gaussian distribution can be specified by a set of parameter $\theta$ comprising a mean and standard deviation (e.g., $\theta=\{\mu,\sigma\}$). Parameter $\theta$ can comprise different parameters for different distributions. When the descriptive feature vector for testing data is distance (e.g., $x^*$) and the target from the training data is dose, the derived conditional probability distribution can be represented by $p(d|x^*,\theta)$ instead of $p(d|x^*)$.

The set of parameters $\theta=\{\mu,\sigma\}$ for the derived conditional probability distribution can be determined by several methods. For example, the parameters can be determined by maximum likelihood (ML), maximum a posteriori (MAP) estimation, computing the posterior predictive distribution by marginalizing over $\theta$, and the like. For ML, a point estimate of $\theta$ can be made by setting $\theta_{ML}^*=\mathrm{argmax}_\theta\, p(d|x^*,\theta)$, resulting in the conditional probability density $p(d^*|\theta_{ML}^*)$, where $d^*$ represents the unobserved dose for a voxel in the testing data. For MAP, a point estimate of $\theta$ can be made by setting:

$$\theta_{MAP}^*=\mathrm{argmax}_\theta p(\theta|x^*,d,\alpha)=\mathrm{argmax}_\theta p(d|x^*,\theta)\,p(\theta|x,\alpha),$$

resulting in the conditional probability density $p(d^*|\theta_{MAP}^*)$. For posterior predictive distribution, the conditional probability can be marginalized over $\theta$, resulting in $p(d^*|x^*,\alpha)=\int p(d^*|\theta)p(\theta|x^*,d,\alpha)d\theta$. MAP and posterior predictive distribution are Bayesian methods, using a prior $p(\theta|x^*,\alpha)$, where $\alpha$ are a set of hyperparameters. Hyperparameters govern the probability distribution of some other parameter. For example, if the conditional distribution is a normal distribution with the variance $\sigma^2$ as the parameter, then a prior distribution describes the probability distribution of the variance. A convenient choice (because it is a conjugate prior) is to assume that the variance follows an inverse Gamma distribution. The inverse Gamma distribution is specified by two parameters, in this context they are referred to as hyperparameters. Bayesian models are a class of statistical models that explicitly incorporate prior information. For example, hierarchical models are a type of Bayesian modeling, wherein features have a hierarchical dependence among each other. In some examples, hierarchical models can be used to model intra-patient features (e.g., texture, tissue oxygenation, and local tumor aggressiveness as dependent on inter-patient features such as gender, age, and anatomical region). Bayesian methods can be more flexible and potentially also more robust, but can come at the cost of additional computational requirements.

The resultant distribution, $p(d^*|\theta^*)$, can specify the unobserved target (e.g., dose in each voxel) of the testing data (e.g., new patient) by the parameters (e.g., θ). In some examples, the resultant distribution parameters (e.g., θ={μ, σ}) represent the therapy model for the testing data. For example, μ can be the expected value of the derived conditional probability distribution.

In other embodiments, the therapy model can be determined by non-parametric density functions (e.g., Gaussian process, Kernel Density Estimation, and the like). In some examples, the therapy probability density functions of voxel dose in the new patent treatment data can follow a Gaussian process. A Gaussian process can contain the set of parameters is θ={μ,Σ} In such a case, the conditional probability p(d*|x,d,x*) can be represented by N(μ,Σ), where the mean μ and covariance Σ are given by:

$$\mu = k(x^*,x)(K(x,x)+\sigma^2 I)^{-1} d$$

$$\Sigma = k(x^*,x^*) - k(x^*,x)(K(x,x)+\sigma^2 I)^{-1} k(x,x^*).$$

The resultant distribution, p(d*|x,d,x*), can specify the target (e.g., dose in each voxel) of the testing data (e.g., new patient) by the parameters (e.g., θ). In some examples, the resultant distribution parameters (e.g., θ={μ,Σ}) represent the therapy model for the testing data.

In other embodiments, the derived conditional probability distribution for the testing data, as described above, can be determined without first determining a training model. In some examples, a discriminative model (e.g., conditional model) directly determines the conditional probability distribution (e.g., p(d*|x*)) using any out of range of machine learning algorithms. Example algorithms include (generalized) linear models, (probabilistic) support vector machines, conditional random fields, artificial neural networks (including deep learning algorithms), and ensemble algorithms (e.g. boosting and random forests). In addition, algorithms that output a point estimate of the target of the testing data (e.g., d*) can be used provided that it is possible to approximate the conditional distribution (e.g., p(d*|x*)) using, for example, a variational approximation, Monte Carlo methods, or dropout (in the case of deep learning).

In some embodiments, the treatment planning system 170 can use the therapy model generated by therapy module 120 and an optimization model to determine an optimal spatial distribution of a derived target vector. In other embodiments, therapy module 120 can generate the therapy model and use the optimization model to generate a treatment plan.

In some embodiments, the optimization model can maximize the total conditional probability p(y|z)=p(y$_1$, . . . , y$_N$|z$_i$, . . . ,z$_N$), where y represents a target vector and z represents a feature vector. When the conditional distribution is log-concave, which means that log(p(z$_i$|y$_i$)) is concave, a globally optimal solution can be found using any gradient descent-type optimization algorithm on the logarithm of the conditional probability (e.g., log(p(y|z))= log(Π$_{i=1}^N$p(y$_i$|z$_i$))=Σ$_{i=1}^N$ log(p(y$_i$|z$_i$))). In some examples, adjacent target elements are assumed to be independent with respect to the feature. The total probability for the optimal spatial distribution thus factorizes into:

$$p(x|y) = \Pi_{i=1}^N p(x_i|y_i).$$

In some embodiments, where the conditional probability distribution is approximated by the therapy model (e.g., mean and standard deviation for a parametric Gaussian function, mean and covariance for a Gaussian process, etc.) the total probability for the optimal spatial distribution can be rewritten as:

$$p(d^*|\theta^*) = \Pi_{i=1}^N p(d_i^*|\theta_i^*).$$

For example, in the case of a parametric Gaussian function, the most probable dose distribution can be found by maximizing the logarithm of the total probability using convex quadratic minimization:

$$\log\left(\prod_{i=1}^N p(d_i^*|\theta_i^*)\right) = \sum_{i=1}^N \log(p(d_i^*|\theta_i^*)) = -\sum_{i=1}^N \frac{1}{2\sigma_i^2}(d_i^* - \mu_i)^2 + \text{constant},$$

where μ is the mean and σ is the standard deviation of the probability density function for the derived conditional probability of the testing data. The expression can be rewritten as:

$$\log(\Pi_{i=1}^N p(d_i^*|\theta_i^*)) = -(d^*(u)-\mu)^T \Lambda (d^*(u)-\mu),$$

where u are the degrees of freedom considered, e.g. the treatment machine's degrees of freedom, and Λ is a diagonal matrix with the entries 1/(2σ$_i^2$) on the main diagonal. Maximizing the optimization problem subject to g(u) and h(u) (e.g., functions that specify equality and inequality constraints imposed upon the solution) yields the optimal spatial dose distribution. In some embodiments, the optimization problem can be solved by general purpose optimization algorithms, such as interior-point methods, sequential quadratic programming (SQP), or augmented Lagrangian methods.

In some examples, the developed treatment plan can be for a patient currently undergoing radiotherapy (e.g., the treatment plan may be updated (adapted) based on current parameters). Alternatively, the developed treatment plan can be for a new patient. The treatment plan can be used by radiotherapy device 150 to perform a treatment in accordance with the treatment plan.

Radiotherapy device 150 delivers a beam or beams of high-energy radiation directed towards a tumor site (or other lesion) in a collimated and controlled manner according to a treatment plan. A multiple-source external-beam radiotherapy device uses a large number of fixed sources, often isotopic sources such as $^{60}$Co which decays via a process including gamma emission. The sources can be mounted in an approximately hemispherical collimator arrangement which collimates each source to direct its radiation to the center of the hemisphere. Thus, at that center point the radiation fluence is very high, whereas away from that point the fluence drops markedly. Individual sources can be blocked or opened to allow irradiation. A patient can therefore be positioned (with all sources blocked), and a selection of sources can then be opened for a specified time to create a high fluence at a specific location within the patient and deliver a specific dose. A tumor might be exposed to several "shots" (which may be at different locations) in order to fill up the target volume with the prescribed dose level. Also, several tumor sites can be treated in one treatment.

Figure 2:
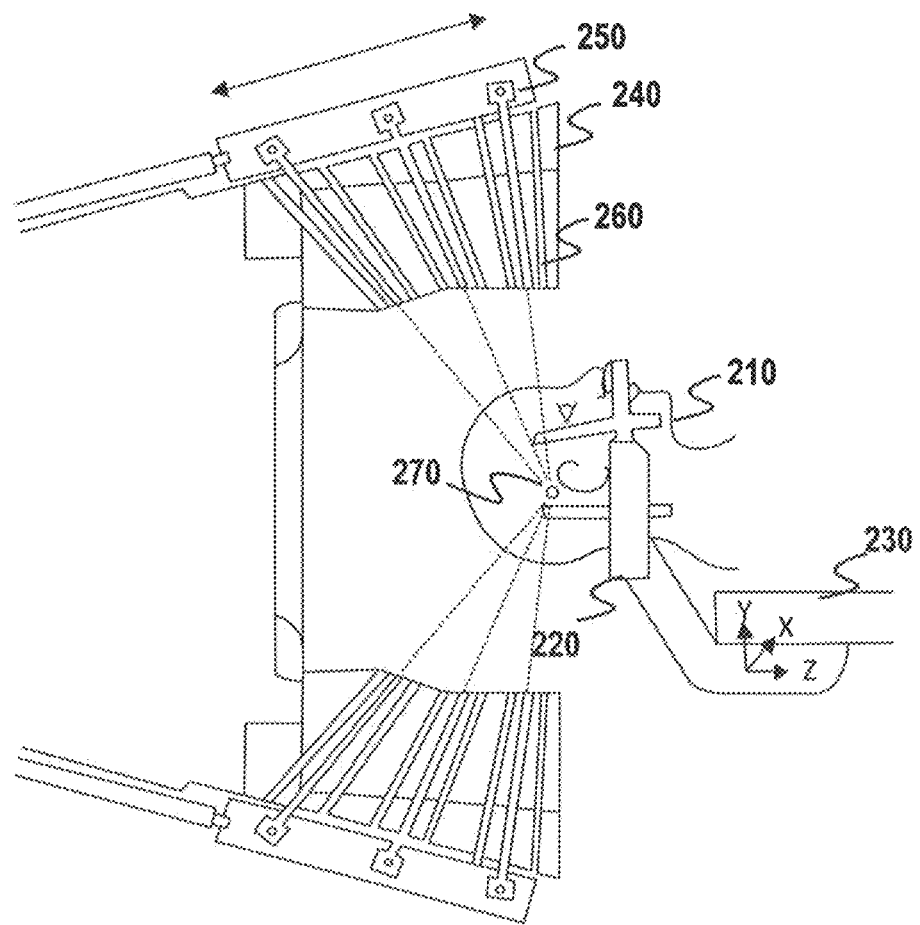
FIG. 2. illustrates an example radiotherapy device, such as a Gamma Knife.

FIG. 2 illustrates an Leksell Gamma Knife 200, one type of multiple-source external-beam type of radiotherapy device 150, according to some embodiments of the present disclosure. As shown in FIG. 2, in a radiotherapy treatment session, a patient 210 may wear a coordinate frame 220 to keep stable the patient's body part (e.g., the head) undergoing surgery or radiotherapy. In some examples, coordinate frame 220 and a patient positioning system 230 establish a spatial coordinate system, which can be used while imaging a patient or during radiation surgery. In some embodiments, radiotherapy device 150 includes a protective housing 240 to enclose a plurality of radiation sources 250. Radiation sources 250 generate a plurality of radiation beams (e.g., beamlets) through beam channels 260. The plurality of radiation beams can be configured to focus on an isocenter 270 from different directions. While each individual radiation beam can have a relatively low intensity, isocenter 270 can receive a relatively high level of radiation when multiple doses from different radiation beams accumulate at isocenter 270. In certain embodiments, isocenter 270 corresponds to a target under surgery or treatment, such as a tumor.

A single-source external-beam radiotherapy device uses a beam of radiation (e.g., in the MeV range, apt to damage tumor cells), and directs the beam towards the patient. The source is movable so as to allow a range of irradiation directions to be chosen, and the lateral extent of the beam is limited by collimating elements so as to match a pattern determined in a predetermined treatment plan, such as the external profile of the tumor or a subsection of it. The direction of the beam is varied so that the tumor is irradiated from multiple directions, thereby reducing the dose delivered to tissue surrounding the tumor site.

Figure 3:
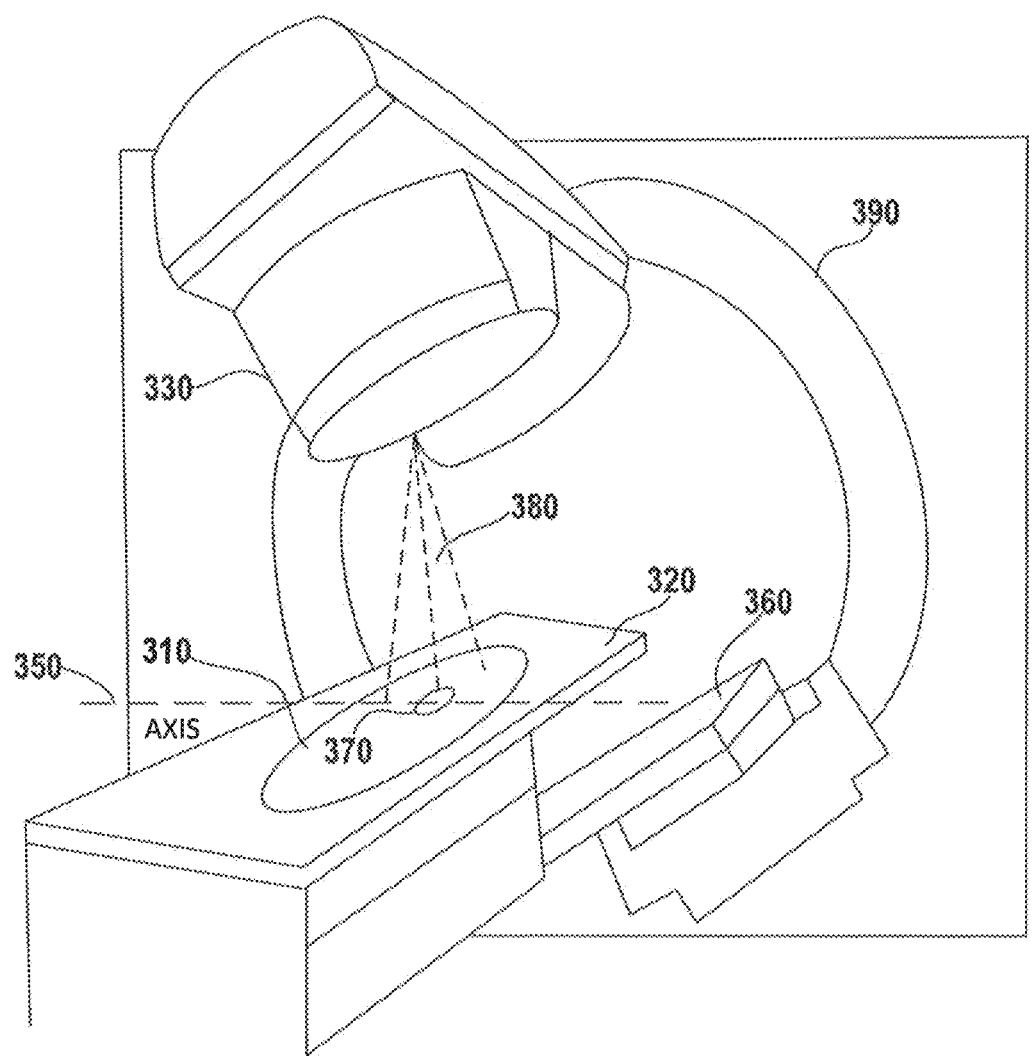
FIG. 3. illustrates another example radiotherapy device, such as a linear accelerator.

FIG. 3 illustrates a linear accelerator 300, a single-source external-beam type of radiotherapy device 150, according to some embodiments of the present disclosure. Using linear accelerator 300, a patient 310 can be positioned on a patient table 320 to receive a radiation dose determined by the treatment plan. In some embodiments, linear accelerator 300 includes a radiation head 330 that generates a radiation beam 340. The entire radiation head 330 can be rotatable around a horizontal axis 350. In some examples, a flat panel scintillator detector 360 is located below the patient table 320, which can rotate synchronously with radiation head 330 around an isocenter 370. The intersection of the axis 350 with the center of the beam 380, produced by the radiation head 330, is usually referred to as "isocenter." The patient table 320 can be motorized so that the patient 310 can be positioned with the tumor site at or close to the isocenter 370. The radiation head 330 can rotate about a gantry 390, to provide patient 310 with a plurality of varying dosages of radiation according to the treatment plan.

Internal radiotherapy (e.g., brachytherapy) involves placing a sealed radiation source in or adjacent to the area requiring treatment. Radiation is then delivered directly to the lesion site. The principal form of control is obtained from the positioning of the source relative to the site, but the source strength parameters can also be controlled using a treatment plan.

Figure 4:
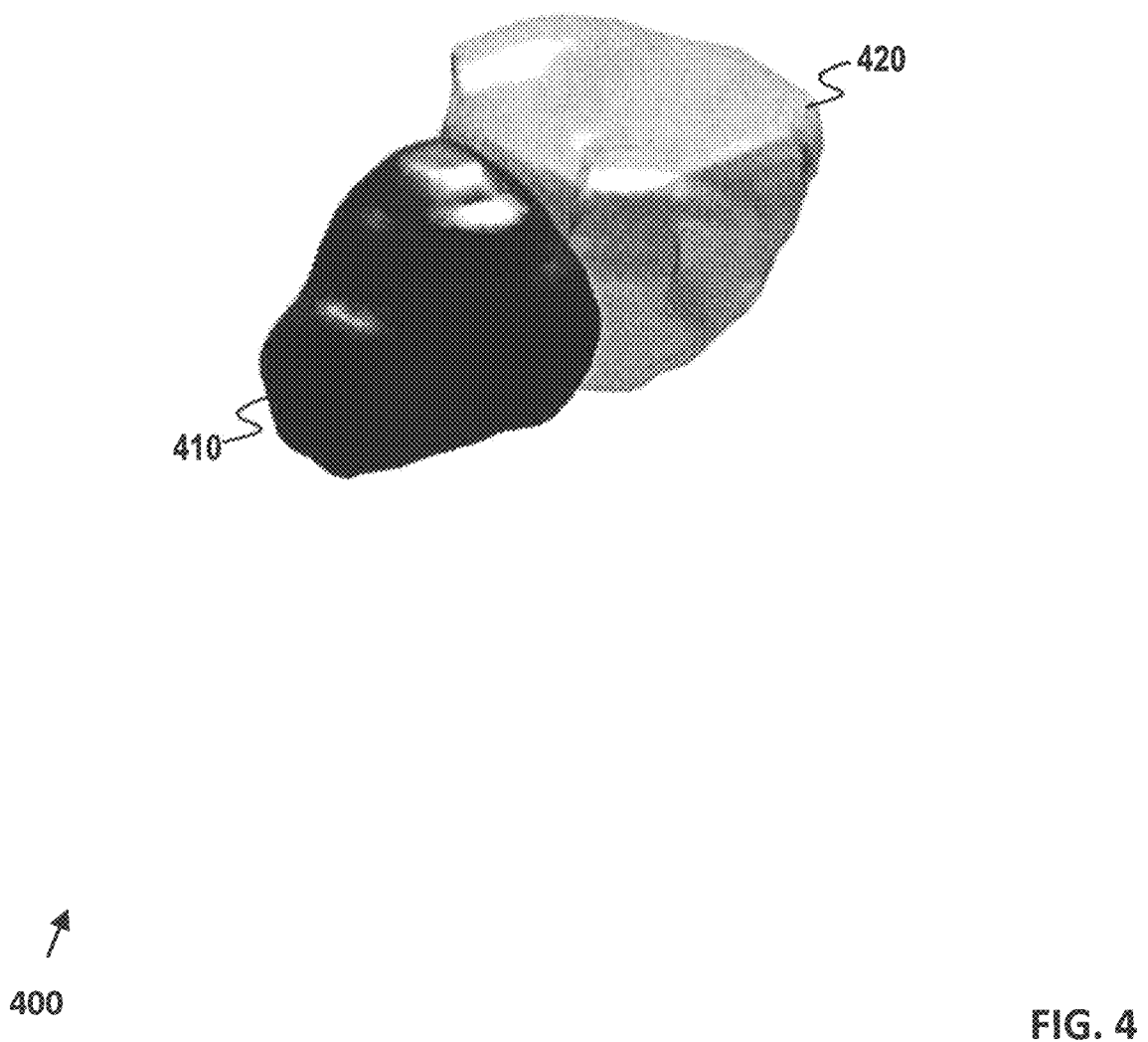
FIG. 4. illustrates exemplary image data showing a target tumor and an OAR.

FIG. 4 illustrates example image data, for example, acquired by image acquisition device 160. In the example, target 410 can be a PTV (e.g., tumor, and the like) and an OAR 420 can be an organ near the target. The PTV can have an irregular volume and may be unique as to its size, shape, and position. In order to delineate the target 410 from the OAR 420, medical images (e.g., MRI images, CT images, PET images, fMRI images, X-ray images, ultrasound images, radiotherapy portal images, SPECT images, and the like) of the patient undergoing radiotherapy can be obtained non-invasively and segmented to include voxels. Each voxel represents a spatial volume in the image data. It is noted that target 410 and OAR 420 shown in FIG. 4 represent a 3D reconstruction of a segmented target and OAR. In some examples, a 3D structure, such as the one shown in FIG. 4, is produced by segmenting image data acquired by image acquisition device 160. For example, instructions stored in treatment planning system 170 may perform a segmentation process to delineate an area, such as a target area or tumor, depicted in the acquired image data. In some embodiments, the delineation of one or more OARs, healthy tissue surrounding the tumor or in close proximity to the PTV, may be required. Therefore, segmentation of the OAR may be performed when the OAR is close to the PTV. For example, the 3D structure can be obtained by contouring the PTV or contouring the OAR within each 2D layer or slice of an image and combining the contour of each 2D layer or slice. The contour can be generated manually (e.g., by a physician, dosimetrist, or health care worker) or automatically (e.g., using a program such as the Atlas-based Autosegmentation software, ABAS®, manufactured by Elekta). In certain embodiments, the 3D structure of a PTV or an OAR can be generated automatically by either training module 110, therapy module 120, and/or stored in training database 130 or testing database 140. In addition, if the PTV is close to the OAR (e.g., prostate in near proximity to the bladder and rectum), segmentation of the OAR can allow study of the dose distribution not only in the PTV, but also in the OAR. In some examples, radiation doses to be applied to a PTV (e.g., a target tumor) and any OAR proximate to the tumor (e.g., left and right parotid, optic nerves, eyes, lens, inner ears, spinal cord, brain stem, and the like) can be determined after segmentation. After the dose is determined for each anatomical structure, Inverse planning can be performed to determine one or more plan parameters, such as volume delineation (e.g., define target volumes, contour sensitive structures), margins around the PTV and OARs, dose constraints (e.g., full dose to the tumor target and zero dose to any OAR; 95% of dose to PTV while spinal cord ≤45Gy, brain stem ≤55Gy, and optic structures <54Gy), beam angle selection, collimator settings, and beam-on times. The result of inverse planning can comprise a radiation therapy treatment plan that can be stored (e.g., in treatment planning system 170, testing database 140, or other storage device). Radiotherapy device 150 can then use the generated treatment plan having these parameters to deliver radiation therapy to a patient.

Figure 5:
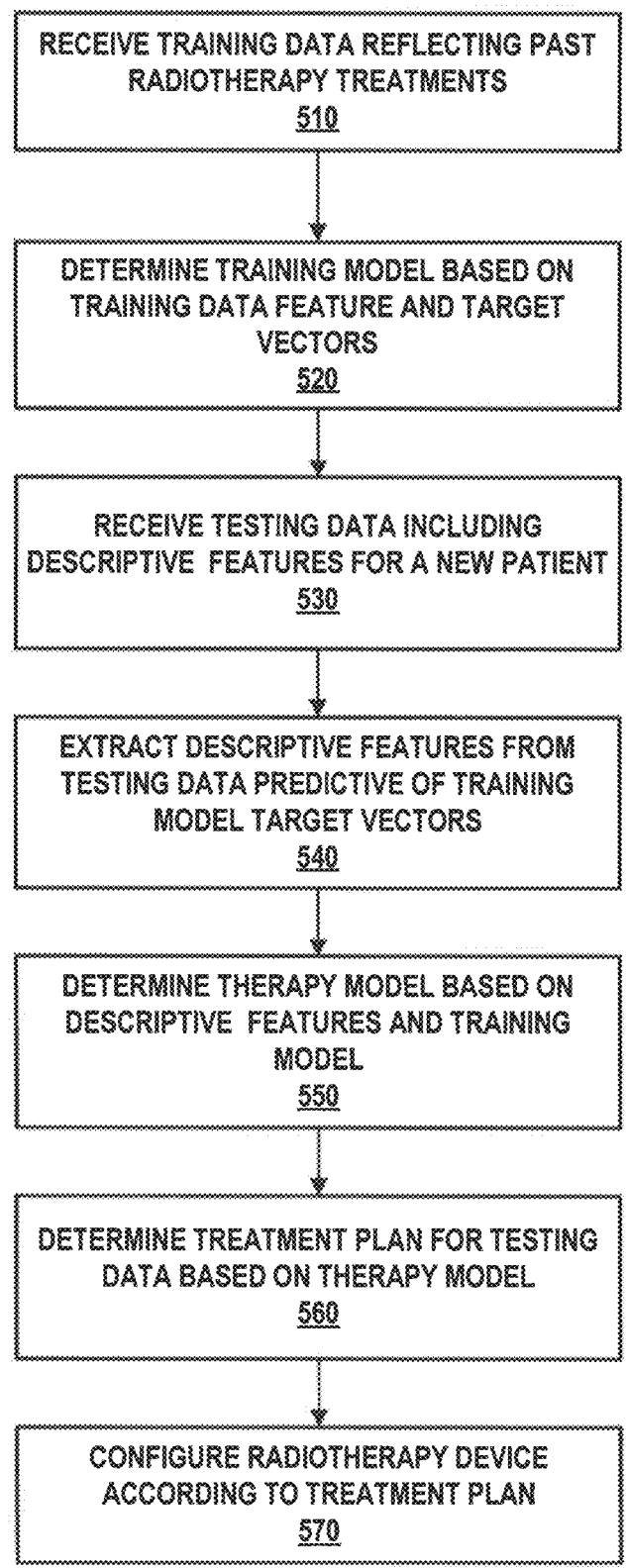
FIG. 5. is a flowchart illustrating an exemplary method of determining a treatment plan for delivering radiation to a patient.

FIG. 5 is a flowchart of an exemplary method 500 of determining an optimized treatment plan for a patient and can be implemented for example in a system shown in FIG. 1. The technologies described herein are consistent with different operating systems or hardware and can be applied in any variety of environments to take advantage of the described features.

At block 510, training data is received as input. In some embodiments, the training module 110 receives the training data from training database 130. The training data can reflect past radiotherapy treatments (e.g., radiation therapy plans delivered prior to the current patient). In some embodiments, the training data reflects treatments of similar to the current patient. For example, previous radiotherapy treatments for prostate cancer can be used as training data for a current patient undergoing prostate cancer treatments.

The training data may or may not be derived from other patients. In some embodiments, training data can be for the same patient. In another embodiment, training data can include treatment plans from other patients with the same or similar medical diagnosis.

At block 520, a training model is determined based on the feature and target vectors of the received training data, as described herein. The target vector can have a conditional probability based on the feature vector, as described herein. For example, the feature can be the signed distance between a voxel in an OAR and the closest boundary voxel in a target for the radiation therapy in the training data. The target vector can be the radiation dose in the voxel of the OAR from which the signed distance is measured.

In some embodiments, the training data are made up of a plurality of past radiotherapy treatment data (e.g., image data and associated dosages for segmented structures in the image).

At block 530, testing data is received as input, for example by therapy module 120. The testing data can be data for a patient that needs a treatment plan to be determined. The testing data can comprise one or more descriptive feature vectors, wherein at least one is similar in nature to the feature vector of the training data and can be descriptive and/or predictive of the target vector. For example, the feature can be the signed distance between a voxel in an OAR and the closest boundary voxel in a PTV for the radiation therapy in the testing data.

At block 540, the descriptive feature vector similar to the feature vector of the training data is extracted from the testing data.

At block 550, a therapy model is determined based on the extracted descriptive feature vector in the testing data and the training model. For example, a training model describing a conditional probability of a dose of radiation at a certain signed distance from a PTV for the training data can be used to determine a new conditional probability of the dose of radiation at the signed distances from a PTV for the testing data. Parameters from a probability density function describing the new conditional probability can be extracted as the therapy model.

At block 560, a treatment plan is determined based on the therapy model. In some embodiments, the treatment plan can be determined based on an output of an optimization model, which uses the therapy model as input. For example, the therapy model can include the mean and standard deviation of a Gaussian distribution and can be used to find the most probable spatial dose distribution for the testing data. Using the therapy model as input to the optimization model yields the dose distribution without iteratively or incrementally approaching an optimal spatial dose distribution solution. The treatment plan can be determined by inverse planning from the optimal spatial dose distribution.

At block 570, a radiotherapy device can be configured according to the treatment plan. In some embodiments, the treatment plan, including the spatial dose distribution, can be used to program radiotherapy device 150 to deliver radiation therapy to the patient. For example, radiation beams can be directed to the patient to obtain the spatial dose distribution in the treatment plan.

Figure 6:
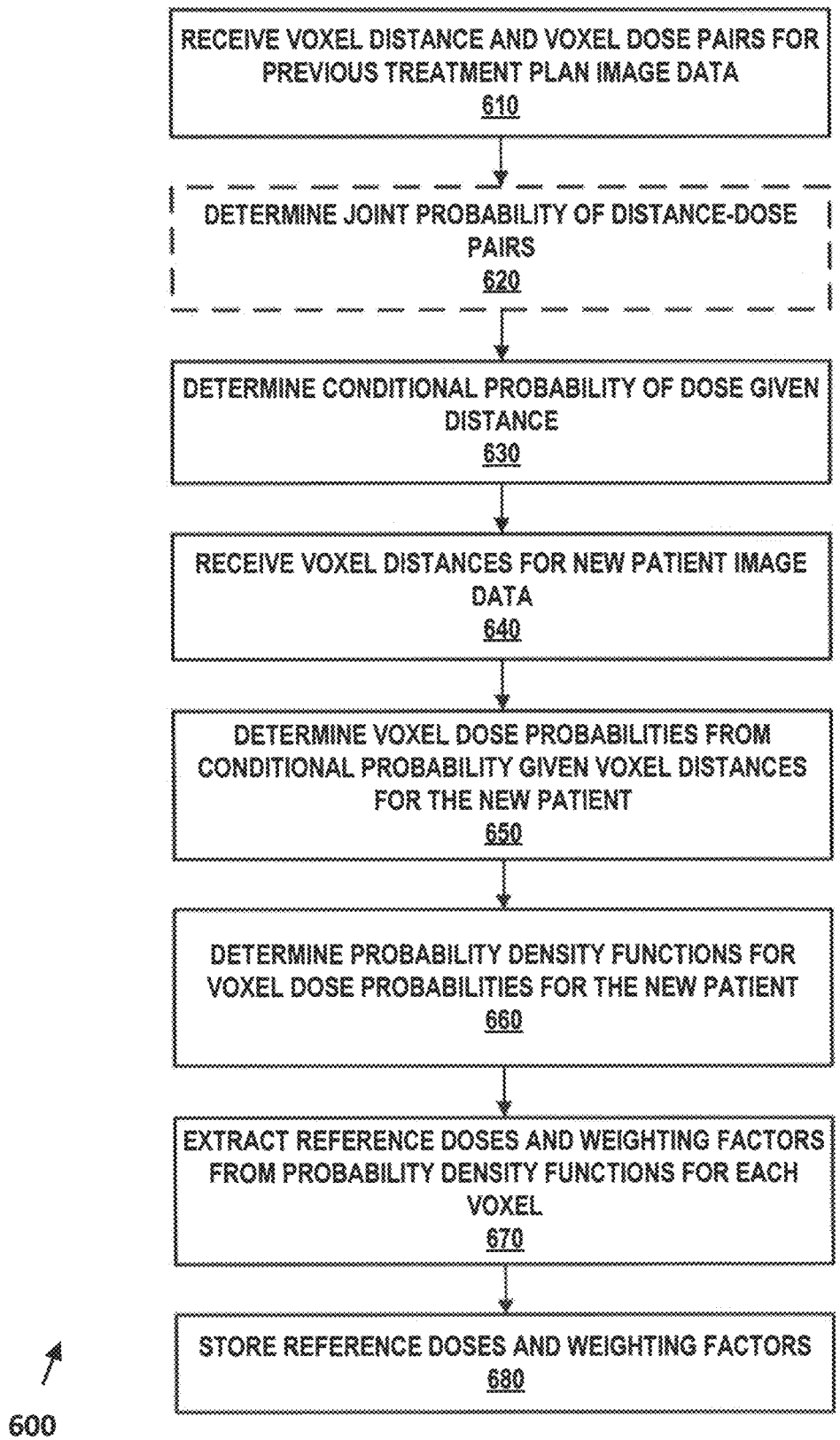
FIG. 6. is a flowchart illustrating an exemplary method of using previous treatment plans to determine reference doses and weighting factors, according to some embodiments of the present disclosure.

FIG. 6 is a flowchart illustrating an exemplary method 600 of determining reference doses and weighting factors (e.g., therapy model) based on voxel distance and voxel dose pairs (e.g., training data) and can be implemented for example in a system shown in FIG. 1. For example, the steps can be performed in training module 110, therapy module 120, and/or treatment planning system 170.

At block 610, voxel distance (x) and voxel dose (d) pairs for previous treatment plan image data (e.g., training data) are received, for example in training module 110. The voxel distance can be a shortest signed distance from a voxel of an OAR to the boundary of a PTV in the treatment plan image data. The voxel dose can be the amount of radiation that the voxel of the OAR received in a previous treatment plan. In this example, the voxel distance can be considered a feature and the voxel dose can be considered a target. The plurality of voxel distances can be a feature vector and the plurality of voxel doses can be a target vector.

At block 620, a joint probability distribution associated with distance-dose pairs can be determined. Determining the joint probability is optional and thus shown by a dashed line. The joint probability can indicate the probability that a certain dose distribution occurs with a certain distance distribution.

At block 630, the conditional probability of a voxel dose given the corresponding distance is determined. In practice, a conditional probability of a voxel dose occurs for each distance. The conditional probabilities can be represented as an array, where each element contains the conditional probability of a voxel dose for a certain distance. The conditional probability of a voxel dose given the corresponding distance can represent a training model.

At block 640, voxel distances for new patient image data (e.g., testing data) are received. In some embodiments, the voxel distances for new patient image data can represent a signed distance $x^*$ from an OAR in the new patient image data and a PTV in new patient image data. In the example, voxel distances for new patient image data represent a descriptive feature of the new patient.

At block 650, voxel dose probabilities for the new patient image data is determined based on the conditional probability of the voxel doses (e.g., training model) in the previous treatment plans and the voxel distances in the new patient image data. For example, substituting $x^*$ for x in the conditional probability $p(d|x)$ immediately yields $p(d|x^*)$. In practice, the probability distribution associated with the distances in the new patient image data, $p(x^*)$, can be different than the probability distribution associated with the distances in the treatment plan image data, $p(x)$. Thus, even though the a substitution of $x^*$ for x can be made, the joint probability $p(x^*, d)$ will be different than $p(x, d)$.

In some embodiments, the conditional probability of the voxel doses in the previous treatment plans can be determined using a Gaussian process. By conditioning on the voxel doses on the signed distance $x^*$ from an OAR, the conditional probability distribution $p(d^*|x, d, x^*)$ can be found.

At block 660, probability density functions are determined for voxel dose probabilities for the new patient. For example, a dose probability distribution (e.g., the conditional probability $p(d^*|x^*)$) may be associated with each voxel distance derived from the new patient image data. As described above, the probability density function can be parametric or non-parametric. In some embodiments, the probability density function can be Gaussian and be represented by a mean and standard deviation. In some examples, the mean can represent a reference dose and the standard deviation can represent a weighting factor. In practice, a reference dose and weighting factor can be determined for each voxel in the new patient image data.

At block 670, the reference doses and weighting factors (e.g., therapy model) are extracted from the probability density functions for each voxel. In some embodiments, the reference doses and weighting factors can represent the moments of the probability density functions.

At block 680, the reference doses and weighting factors are stored (e.g., in memory, training database 130, testing database 140, treatment planning system 170, and/or OIS 180) for later use. In some embodiments, the reference doses and weighting factors can be transferred to therapy module 120 for further processing.

As described above, the reference doses and weighting factors can represent parameters of probability density functions derived from previous treatment plan image data and new patient image data. In other examples, the parameters of probability density functions derived from other feature and target vectors from training data and descriptive features from testing data can be determined. As described above, probability distributions are obtained for a plurality of doses and distances. Therefore, spatial resolution of the data can be maintained.

Figure 7:
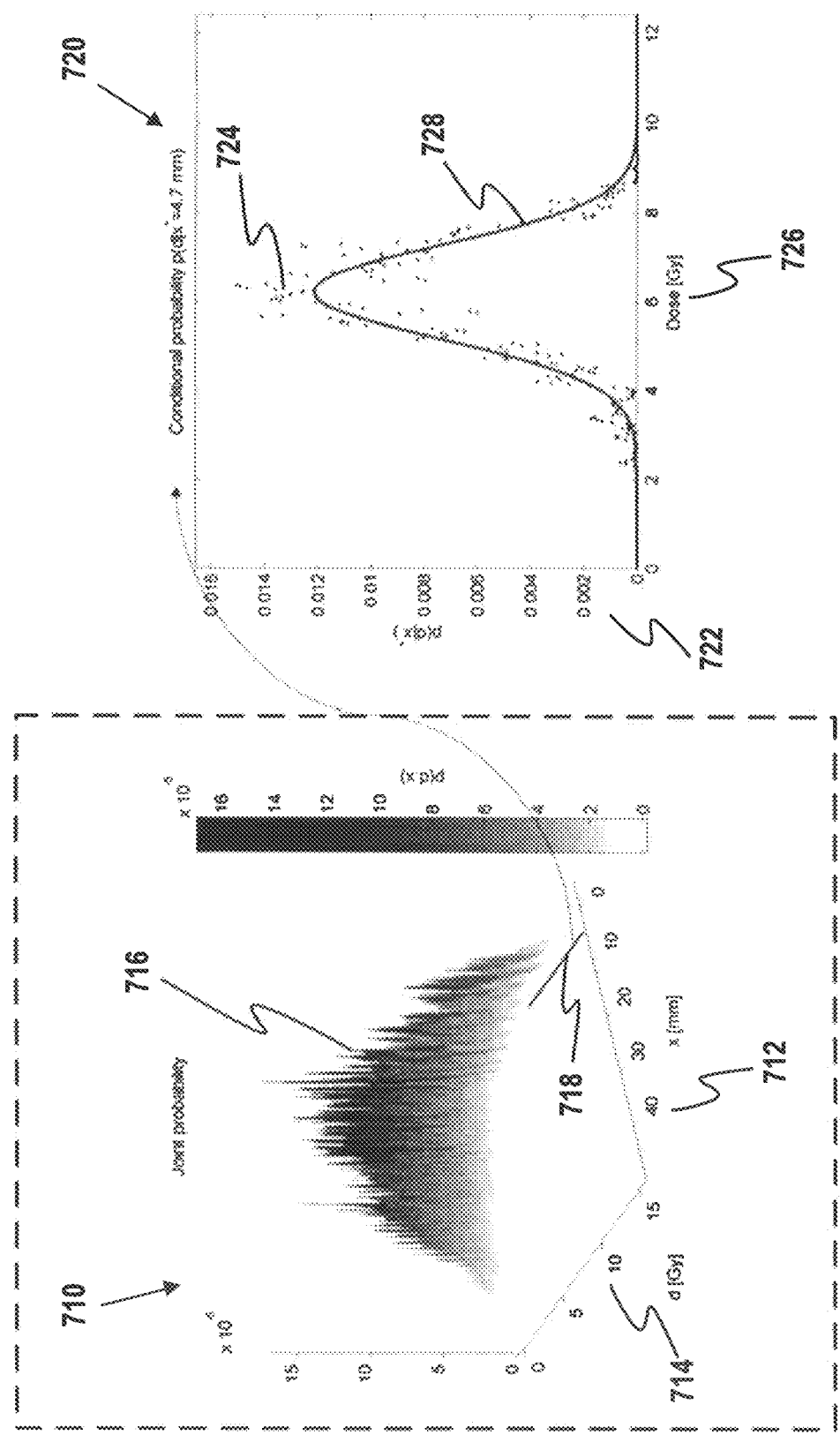
FIG. 7. illustrates an example of using a training model from training data to generate a therapy model for testing data, according to some embodiments of the present disclosure.

FIG. 7 illustrates an example 700 of using a training model from training data to generate a therapy model for testing data. For example, the steps can be performed in training module 110, therapy module 120, and/or treatment planning system 170. In some embodiments, joint probability distribution 710 can be determined from training data. A conditional probability 720 can be determined from the joint probability. In some embodiments, conditional probability 720 can be determined directly from training data, therefore determining joint probability 710 is optional and shown in a dashed box.

In the example shown, training data comprise a feature vector with elements representing a distance 712 (e.g., signed distance from an OAR to a PTV) and a target vector with elements representing a radiation dose 714. In some examples, the distance 712 can be given in millimeters (mm) and, for example, be between 0 and 50 mm. In some examples, the distance can be signed and include negative distances. In some examples, the dose 714 can be given in Grays (Gy) and, for example, be between 0 and 15 Gy. The joint probability 710 shows the probability 716 of a certain dose occurring at a certain distance. In practice, each distance 712 can be represented by a conditional probability by taking all dose probabilities 714 along a line 718. In some embodiments, the conditional probability can be a training model. This conditional probability represents the probability that a certain dose is present in the training data for a given distance. In the example shown, line 718 indicates a distance of 4.7 mm.

In some embodiments, testing data can also comprise a feature vector with elements representing a distance (e.g., signed distance from an OAR to a PTV). The probability that a certain distance is present in the testing data can be different than the probability that a distance is present in the testing data. In some examples, conditional probability 720 can be determined for each distance present in the testing data. Conditional probability 720 can thus be a "slice" of the joint probability. Conditional probability $p(d|x^*)$ 722 thus represents the dose distribution 724 from the training data for a distance present in the testing data. Dose distribution 724 represents the probability of a given dose 726 is present at the specified distance. In practice, not all distances in the training data may be present in the testing data and vice versa. In the case that the testing data does not include a distance present in the testing data, that dose distribution is not used. If the training data does not include a distance that is present in the testing data, interpolation and/or extrapolation can be performed to determine a dose distribution at that distance.

In some embodiments, dose distribution 724 can be approximated by a parametric probability density function 728. In other embodiments, probability density function 728 can be non-parametric. In some examples, probability density function 728 can be represented by its moments. The moments can be a therapy model. In the example shown, the probability density function 728 is a Gaussian function of a normally distributed dose with a mean of 6.21 Gy and standard deviation of 1.05 Gy.

Figure 8:
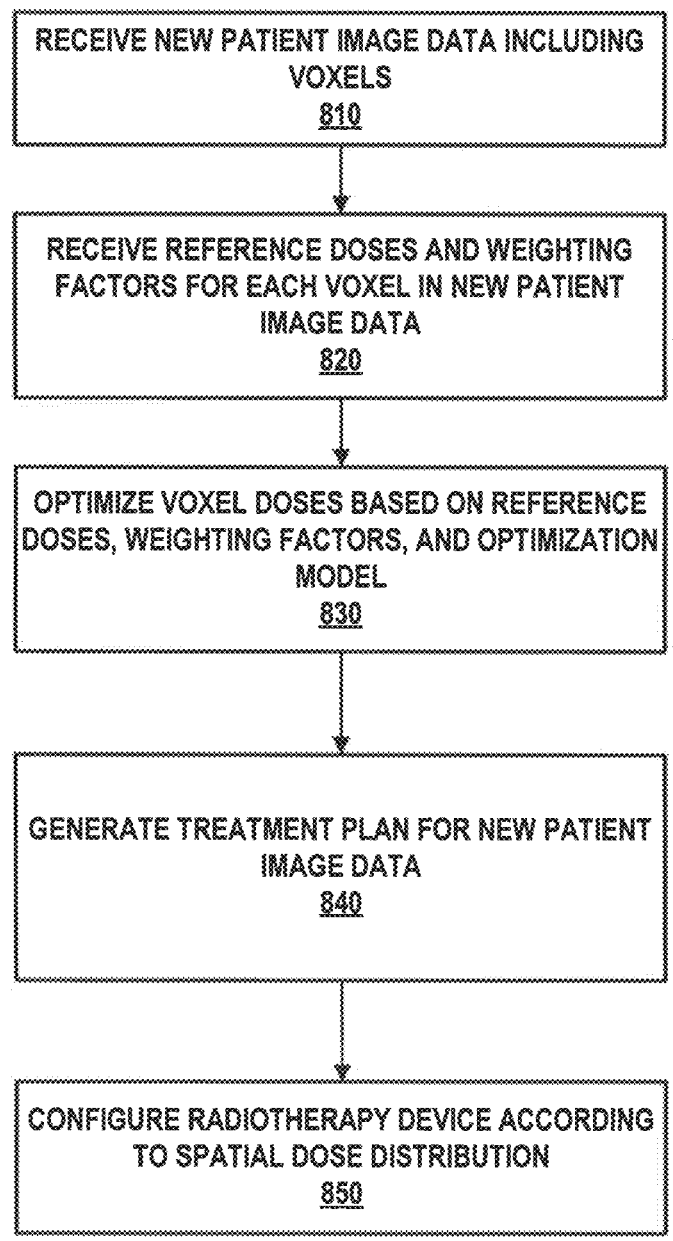
FIG. 8. is a flowchart illustrating an exemplary method of using reference doses and weighting factors to generate a spatial dose distribution, according to some embodiments of the present disclosure.

FIG. 8 is a flowchart illustrating an exemplary method 800 of utilizing reference doses and weighting factors (e.g., therapy model) to generate an optimal spatial dose distribution and can be implemented for example in a system such as shown in FIG. 1. For example, the steps can be performed in training module 110, therapy module 120, and/or treatment planning system 170. Once the reference doses and weighting factors are obtained, for example as shown in method 600, they can be used, for example in therapy module 120 to generate an optimal probability density associated with the target vector, or a target element, for the development of a new treatment plan.

At block 810, new patient image data including voxel information can be received. The new patient image data can be testing data obtained from, for example, an image acquisition device 160.

At block 820, reference doses and weighting factors describing a conditional probability distribution of the new patient is received. In some embodiments, the parameters can be generated by the method 600. In some examples, the parameters describe the probability of a target element given a feature element (e.g., mean and standard deviation of a dose in each voxel of the patient).

At block 830, and optimal dose distribution for the testing data is generated based on the reference doses and weighting factors. In some embodiments, optimization can be achieved using an optimization model, as described herein.

In an embodiment, generating the optimal dose distribution can allow for the validation of a previously determined treatment plan. For example, the optimal spatial dose distribution can allow for the validation of one or more previously generated treatment plans with the newly generated treatment plan for the purposes of quality assurance or training.

At block 840, a treatment plan is generated for the new patient image data. As described above, inverse planning can be used to generate the treatment plan from the optimal spatial dose distribution.

Figure 9:
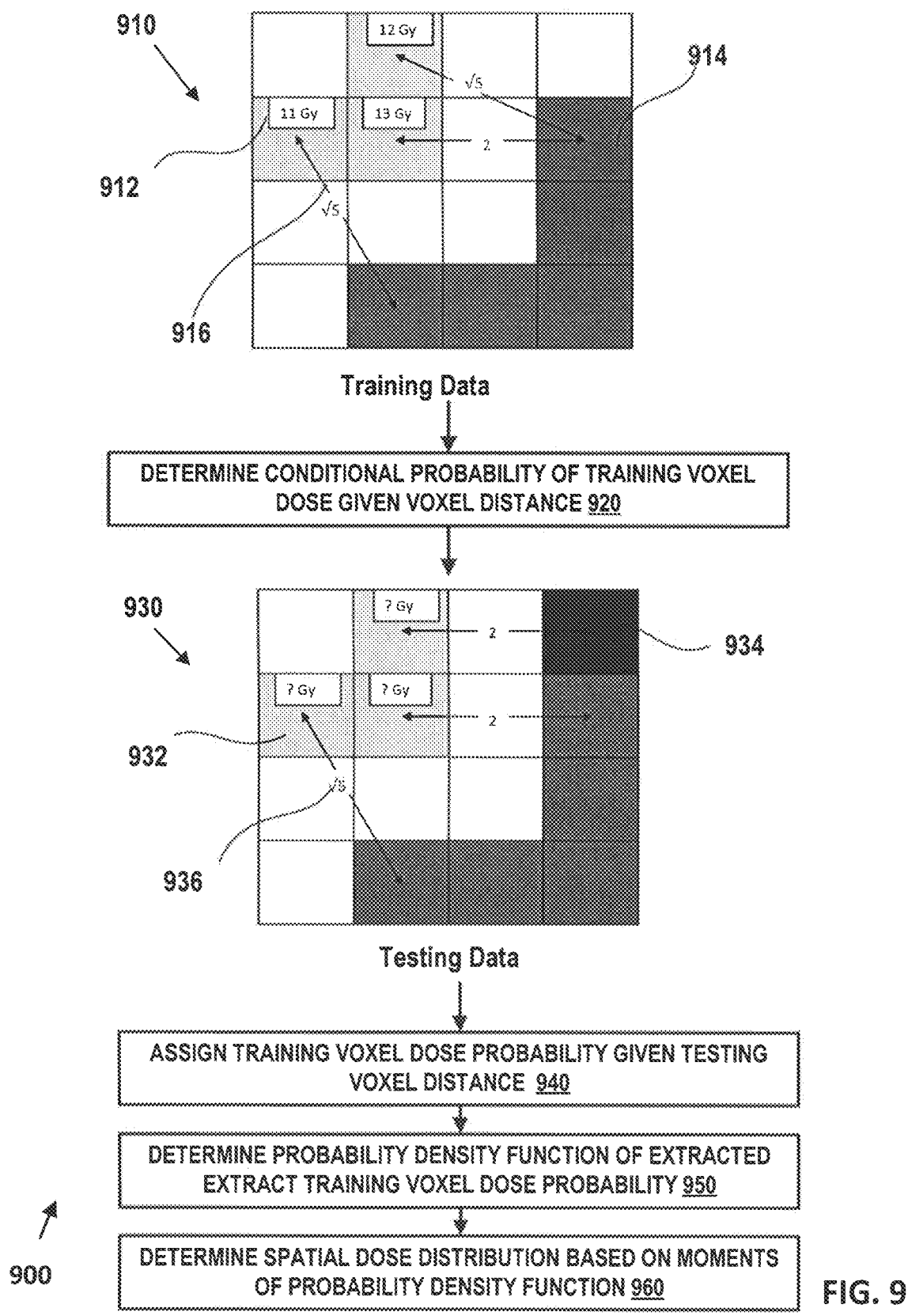
FIG. 9. illustrates an example using OAR distance as a feature vector in determining a spatial dose distribution, according to some embodiments of the present disclosure.

FIG. 9 illustrates an example 900 of using distance of an OAR to a PTV as a feature vector in determining an optimized treatment plan, can be implemented for example in a system such as shown in FIG. 1. For example, the steps can be performed in training module 110, therapy module 120, and/or treatment planning system 170.

In the example, training data 910 represents simplified image data from a past treatment plan with OAR voxels 912 and PTV voxels 914. A singed distance 916 ($x$) can be determined from an OAR voxel 912 to the closest PTV voxel 914. Furthermore, each OAR voxel 912 can have a radiation dose (d) associated with it. In the example, OAR voxels are a distance of $\sqrt{5}$ and 2 voxels from PTV voxels. Voxels that are $\sqrt{5}$ away from the PTV contain doses of 11 Gy and 12 Gy, while a single voxel a distance of 2 away from PTV contains 13 Gy.

At 920, a conditional probability can be determined given the example training voxel doses and distances. As described herein, a conditional probability can be determined from a joint probability of a feature and target and the probability of the feature, given by $p(d|x)=p(x, d)/p(x)$. In this case, the joint probability contains the following elements:

$$p_{x,d}(2, 13)=⅓, \quad p_{x,d}(2, 12)=0, \quad p_{x,d}(2, 11)=0, \quad p_{x,d}(\sqrt{5}, 13)=0, p_{x,d}(\sqrt{5}, 12)=⅓, p_{x,d}(\sqrt{5}, 11)=⅓$$

The probability distribution for the distance contains the elements:

$$p_x(2)=⅓, p_x(\sqrt{5})=⅔$$

The resultant conditional probability for the example has the following elements:

$p_{x,d}(13, 2)=1$, $p_{x,d}(12, 2)=0$, $p_{x,d}(12, 2)=0$, $p_{x,d}(13|\sqrt{5})=0$, $p_{x,d}(12|\sqrt{5})=\frac{1}{2}$, $p_{x,d}(11|\sqrt{5})=\frac{1}{2}$ In the example, testing data 930 represents simplified image data for a new patient with OAR voxels 932 and PTV voxels 934. A singed distance 936 (x*) can be determined from an OAR voxel 932 to the closest PTV voxel 934. Furthermore, each OAR voxel 932 can have a radiation dose (d*) associated with it (shown as ? Gy in the figure). In the example, OAR voxels are a distance of sqrt(5) and 2 voxels from PTV voxels. Testing data 930 does not have radiation doses associated with the OAR voxels. Furthermore, testing data 930 contains one more voxel of PTV and does the training data 910. As a result, distance probabilities for testing data 930 are ⅔ for the distance of 2 and ⅓ for distance sqrt(5).

At 940, training voxel dose probabilities (e.g., conditional probabilities) are assigned to testing data OAR voxels based on the testing data OAR voxel distances. Thus, two of the voxels in the example are assigned the probability distribution for a distance of 2, and the third voxel is assigned the probability distribution for a distance of $\sqrt{5}$.

At 950, probability density functions for each OAR voxel are determined. In this simplified example, only a single training datum is used. In practice, a plurality of training data can be used to develop more complete voxel dose probabilities. In the example, Gaussian probability density functions can be determined. For example, voxel dose probabilities for voxels with a distance of 2 would have a mean of 13 Gy and standard deviations of 0 Gy. The voxel dose probability for the voxel with a distance of $\sqrt{5}$ would have a mean of 11.5 Gy and standard deviation of 0.707 Gy.

At 960, a spatial dose distribution can be determined based on the moments of the probability density function for each voxel. In the example, the means and standard deviations of doses for each voxel are the moments of the Gaussian density function. As described herein, an optimization model can be used with the moments to determine the spatial dose distribution.

Figure 10:
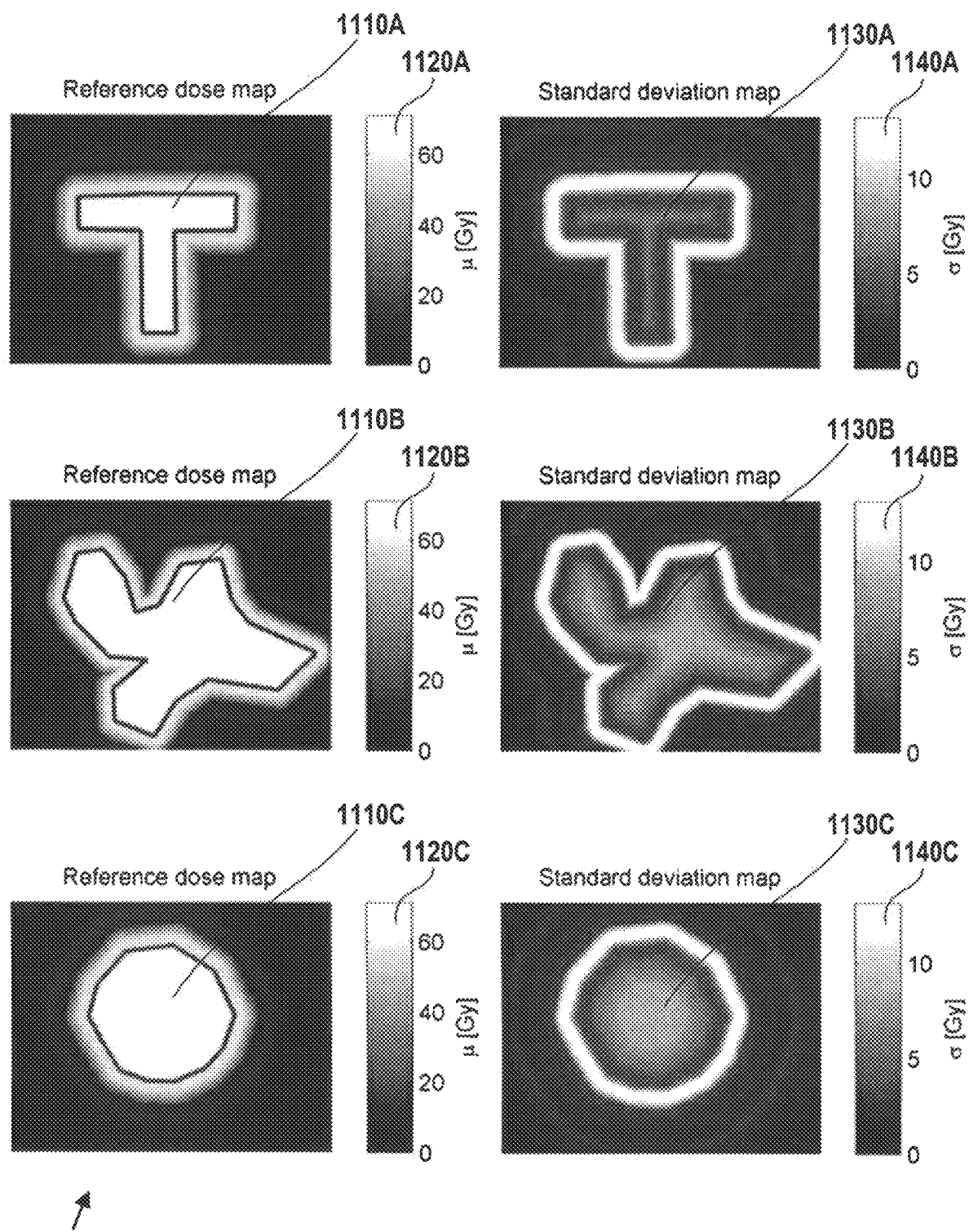
FIG. 10. illustrates examples of parameters generated according to some embodiments of the present disclosure.

FIG. 10 illustrates example implementations 1000 of reference doses and standard deviations. For example, reference doses and standard deviations can be generated by therapy module 120. The example shows reference dose maps 1010A, 1010B, and 1010C for three different OARs. The reference dose maps 1010A, 1010B, and 1010C show the means 1020A, 1020B, and 1020C for example Gaussian distributions. The example also shows standard deviation maps 1030A, 1030B, and 1030C for three different OARs. The standard deviation maps 1030A, 1030B, and 1030C show the standard deviations 1040A, 1040B, and 1040C for example Gaussian distributions.

The technologies described herein have many advantages in the field of radiation therapy or radiotherapy. For example, determining a treatment plan as described herein can significantly reduce computational time and required memory.

Aspects of the embodiments and any of the methods described herein can be performed by computer-executable instructions stored in one or more computer-readable media (storage or other tangible media) or stored in one or more compute readable storage devices, as described herein. The computer-executable instructions can be organized into one or more computer-executable components or modules. Aspects of the embodiments can be implemented with any number and organization of such components or modules. For example, aspects of the disclosed embodiments are not limited to the specific computer-executable instructions or the specific components or modules illustrated in the figures and described herein. Other embodiments may include different computer-executable instructions or components having more or less functionality than illustrated and described herein.

The order of execution or performance of the operations in the disclosed embodiments illustrated and described herein is not essential, unless otherwise specified. That is, the operations can be performed in any order, unless otherwise specified, and embodiments can include additional or fewer operations than those disclosed herein. For example, it is contemplated that executing or performing a particular operation before, contemporaneously with, or after another operation is within the scope of aspects of the disclosed embodiments.

Having described the disclosed embodiments in detail, it will be apparent that modifications and variations are possible without departing from the scope of aspects as defined in the appended claims. For instance, elements of the illustrated embodiments may be implemented in software and/or hardware. In addition, the technologies from any embodiment or example can be combined with the technologies described in any one or more of the other embodiments or examples. In view of the many possible embodiments to which the principles of the disclosed technology may be applied, it should be recognized that the illustrated embodiments are examples of the disclosed technology and should not be taken as a limitation on the scope of the disclosed technology. Therefore, it is intended that all matter contained in the above description and shown in the accompanying drawings shall be interpreted as illustrative and not in a limiting sense.

What is claimed is:

1. A method for generating a treatment plan for a patient, the method comprising:
   receiving training data reflecting radiotherapy treatment data, wherein the training data includes:
      a training feature vector including data generated from a plurality of training medical images, the training feature vector including image data of a first region of each of the training medical images and image data of a second region of each of the training medical images, and
      a training target vector including at least one of treatment plan outcome or a radiotherapy session parameter;
   determining a training model, wherein determining the training model comprises:
      obtaining, from the training feature vector, signed distances of the training medical images, each signed distance reflecting a minimum distance between a non-target tissue of a subject in the first region of a given one of the training medical images and a boundary of a target volume of the subject in the second region of the given one of the training medical images,
      obtaining, from the training target vector, radiotherapy dose data reflecting radiation doses delivered to the non-target tissues in the first regions of the training medical images, and
      for each signed distance of the training feature vector, determining conditional probabilities of delivering the radiation doses corresponding to the radiotherapy dose data to a non-target tissue having a minimum distance from a boundary of a target volume that is equal to the signed distance;

receiving testing data associated with the patient, wherein the testing data includes a descriptive feature vector that comprises a signed distance of the patient reflecting a minimum distance between a non-target tissue of the patient in a first region of a testing medical image and a boundary of a target volume of the patient in a second region of the testing medical image;

determining a therapy model, wherein determining the therapy model comprises:
- identifying one of the signed distances in the training feature vector that is equal to the signed distance of the patient, and
- determining a distribution of the conditional probabilities of the identified signed distance and determining the therapy model based on the distribution;

generating the treatment plan for the testing data based on the therapy model, the treatment plan indicating a radiation dose of the target volume of the patient; and delivering radiation to the patient according to the generated treatment plan.

2. The method of claim 1, further comprising validating a previous treatment plan based on the generated treatment plan.

3. The method of claim 1, wherein determining the training model comprises:
- selecting a specific feature type that includes the signed distances of the training feature vector and a specific target type that includes the radiotherapy dose data from the received training data, wherein the specific feature type is predictive of the specific target type;
- aggregating feature vectors of the selected feature type and target vectors of the specific target type across a plurality of training data; and
- determining a conditional probability for the aggregated target vectors based on the aggregated feature vectors.

4. The method of claim 1, wherein:
- each signed distance of the training feature vector is a signed distance reflecting a minimum distance from a first voxel in one of the training medical images corresponding to the non-target tissue of the subject to a plurality of second voxels in the one of the training medical images corresponding to the boundary of the target volume of the subject, and
- the radiotherapy dose data reflects a radiation dose delivered to the non-target tissue of the subject corresponding to the first voxel.

5. The method of claim 1, further comprising:
segmenting the plurality of training medical images to delineate structures in the plurality of training medical images, wherein segmenting the plurality of training medical images includes segmenting a first training medical image to delineate the non-target tissue of the subject in the first training medical image and the boundary of the target volume of the subject in the first training medical image.

6. The method of claim 1, wherein:
the training data includes at least one of previous treatment plans of the patient or treatment plans of previous patients,
the target volume of the subject in at least one of the training medical images corresponds to a planned radiotherapy target volume of a previous radiotherapy session, and
the non-target tissue of the subject in the at least one of the training medical images corresponds to tissue outside of the planned radiotherapy target volume of the previous radiotherapy session.

7. The method of claim 1, wherein determining the therapy model comprises:
- determining a conditional probability of the training target vector based on the descriptive feature vector, the conditional probability indicating a probability of delivering one of the radiation doses corresponding to the radiotherapy dose data to the non-target tissue of the patient;
- determining a probability density function representing the conditional probability; and
- extracting parameters of the probability density function.

8. The method of claim 1, wherein generating the treatment plan for the patient comprises minimizing a convex optimization function based on the therapy model to determine one or more treatment plan parameters.

9. A radiotherapy system comprising:
a memory storing computer executable instructions;
at least one processor device communicatively coupled to the memory, wherein the at least one processor device is configured to execute the computer executable instructions to:
- receive training data reflecting radiotherapy treatment data, wherein the training data includes:
  - a training feature vector including data generated from a plurality of training medical images, the training feature vector including image data of a first region of each training medical image and image data of a second region of each training medical image, and
  - a training target vector including at least one of a treatment plan outcome or a radiotherapy session parameter;
- determine a training model, wherein determining the training model comprises:
  - obtaining, from the training feature vector, signed distances of the training medical images, each signed distance reflecting a minimum distance between a non-target tissue of a subject in the first region of a given training medical image and a boundary of a target volume of the subject in the second region of the given training medical image,
  - obtaining, from the training target vector, radiotherapy dose data reflecting radiation doses delivered to the non-target tissues in the first regions of the training medical images, and
  - for each signed distance of the training feature vector, determining conditional probabilities of delivering the radiation doses corresponding to the radiotherapy dose data to a non-target tissue having a minimum distance from a boundary of a target volume that is equal to the signed distance;
- receive testing data associated with a patient, wherein the testing data includes a descriptive feature vector that comprises a signed distance of the patient reflecting a minimum distance between a non-target tissue of the patient in a first region of a testing medical image and a boundary of a target volume of the patient in a second region of the testing medical image;

determine a therapy model, wherein determining the therapy model comprises:
  identifying a signed distance in the training feature vector that is equal to the signed distance of the patient, and
  determining a distribution of the conditional probabilities of the identified signed distance and determining the therapy model based on the distribution; and
generate a treatment plan for the testing data based on the therapy model, the treatment plan indicating a radiation dose of the target volume of the patient; and
a radiotherapy device configured to use the generated treatment plan to deliver radiation to the patient.

10. The radiotherapy system of claim 9, wherein the therapy model comprises parameters of a parametric estimation of a conditional probability.

11. The radiotherapy system of claim 9,
wherein the at least one processor device is further configured to generate the treatment plan based on the therapy model and an optimization model, and
wherein the generated treatment plan includes parameters specifying at least one of beam angle selection, collimator settings, or beam-on times of the radiotherapy device.

12. The radiotherapy system of claim 9, wherein the at least one processor device is further configured to validate a previous treatment plan based on the generated treatment plan.

13. The radiotherapy system of claim 9, wherein the training data comprise a training sample and the training sample comprises a feature and a target of the training data.

14. The radiotherapy system of claim 9, wherein the testing data comprise a testing sample and the testing sample comprises a descriptive feature of the testing data.

15. The radiotherapy system of claim 9, wherein:
each signed distance of the training feature vector is a signed distance reflecting a minimum distance from a first voxel in one of the training medical images corresponding to the non-target tissue of the subject to a plurality of second voxels in the one of the training medical images corresponding to the boundary of the target volume of the subject, and
the radiotherapy dose data reflects a radiation dose delivered to the non-target tissue of the subject corresponding to the first voxel.

16. One or more computer-readable storage devices having computer-executable instructions stored thereon causing a processor device to perform a method for generating a treatment plan for a patient, the method comprising:
receiving training data reflecting therapy treatment data, wherein the training data includes:
  a training feature vector including data generated from a plurality of training medical images, the training feature vector including image data of a first region of each training medical image and image data of a second region of each training medical image, and
  a training target vector including at least one of a treatment plan outcome or a radiotherapy session parameter;
selecting a specific feature type from the received training data, wherein the specific feature type includes signed distance data reflecting a minimum distance between a non-target tissue of a subject in the first region of a given training medical image and a boundary of a target volume of the subject in the second region of the given training medical image;
selecting a specific target type from the received training data, wherein the specific target type includes radiotherapy dose data reflecting radiation doses delivered to the non-target tissues in the first regions of the training medical images and wherein the specific feature type is predictive of the specific target type;
aggregating feature vectors of the specific feature type and target vectors of the specific target type across a plurality of the received training data, the aggregated feature vectors including the signed distances of the training medical images and the aggregated target vectors including the radiation doses delivered to the non-target tissues in the first regions of the training medical images;
for each signed distance of the aggregated feature vectors, determining conditional probabilities of delivering the radiation doses corresponding to the aggregated target vectors to a non-target tissue arranged at a location corresponding to the signed distance;
receiving testing data associated with the patient, wherein the testing data includes a descriptive feature vector that comprises signed distance data of the patient reflecting a minimum distance between a non-target tissue of the patient in a first region of a testing medical image and a boundary of a target volume of the patient in a second region of the testing medical image;
identifying one of the signed distances of the aggregated feature vectors that is equal to the signed distance of the patient;
determining a probability density function based on the conditional probabilities of the identified signed distance;
extracting parameters of the probability density function;
minimizing a convex optimization function based on the parameters of the probability density function to determine one or more parameters of a treatment plan, the treatment plan indicating a radiation dose of the target volume of the patient; and
delivering radiation to the patient according to the one or more parameters of the treatment plan.

17. The one or more computer-readable storage devices of claim 16, wherein the training data includes at least one of previous treatment plans of the patient or treatment plans of previous patients.

18. The one or more computer-readable storage devices of claim 16, wherein:
the signed distance data includes signed distance data reflecting a minimum distance from a first voxel in one of the training medical images corresponding to the non-target tissue of the subject to a plurality of second voxels in the one of the training medical images corresponding to the boundary of the target volume of the subject, and
the radiotherapy dose data reflects a radiation dose delivered to the non-target tissue of the subject corresponding to the first voxel.

* * * * *